(12) United States Patent
Li et al.

(10) Patent No.: US 9,502,671 B2
(45) Date of Patent: Nov. 22, 2016

(54) TRIDENTATE CYCLOMETALATED METAL COMPLEXES WITH SIX-MEMBERED COORDINATION RINGS

(71) Applicant: Arizona Board of Regents on behalf of Arizona State University, Scottsdale, AZ (US)

(72) Inventors: Jian Li, Tempe, AZ (US); Zhi-Qiang Zhu, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/808,190

(22) Filed: Jul. 24, 2015

(65) Prior Publication Data

US 2016/0028029 A1 Jan. 28, 2016

Related U.S. Application Data

(60) Provisional application No. 62/029,737, filed on Jul. 28, 2014.

(51) Int. Cl.
*C07F 15/00* (2006.01)
*C09K 11/06* (2006.01)
(Continued)

(52) U.S. Cl.
CPC ....... *H01L 51/0087* (2013.01); *C07F 15/0086* (2013.01); *C09K 11/06* (2013.01);
(Continued)

(58) Field of Classification Search
CPC ........... H01L 51/0087; H01L 51/5016; C07F 15/0086; C09K 11/06; C09K 2211/185; C09K 2211/1074
USPC .......................................................... 546/4
See application file for complete search history.

(56) References Cited

U.S. PATENT DOCUMENTS 6,824,895 B1 * 11/2004 Sowinski ............... C09K 11/06
 313/504
7,026,480 B2   4/2006  Che et al.
(Continued)

FOREIGN PATENT DOCUMENTS

JP   2006282965 A   10/2006
JP   2006114889 A   12/2008
(Continued)

OTHER PUBLICATIONS

Tani; Journal of Organometallic Chemistry 2004, 689, 1665-1674.*
(Continued)

*Primary Examiner* — Noble Jarrell
*Assistant Examiner* — Daniel Carcanague
(74) *Attorney, Agent, or Firm* — Fish & Richardson P.C.

(57) ABSTRACT

Tridentate cyclometalated complexes with rigid six-membered coordination rings of General Formula I having tunable emission wavelengths in the visible range. These emitters are suitable for full color displays and lighting applications.

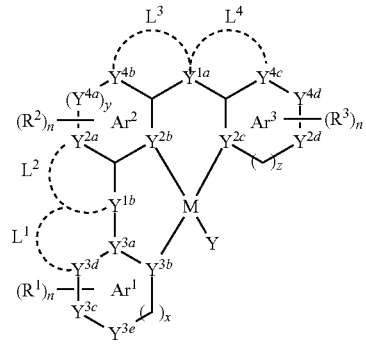

General Formula I

17 Claims, 2 Drawing Sheets

(51) Int. Cl.
  *H01L 51/00* (2006.01)
  *H01L 51/50* (2006.01)
  *H01L 51/42* (2006.01)
(52) U.S. Cl.
  CPC .......... *C09K2211/1029* (2013.01); *C09K 2211/1044* (2013.01); *C09K 2211/185* (2013.01); *H01L 51/42* (2013.01); *H01L 51/5016* (2013.01); *Y02E 10/549* (2013.01)

(56) References Cited

U.S. PATENT DOCUMENTS

| | | | |
|---|---|---|---|
| 7,029,766 | B2 | 4/2006 | Huo et al. |
| 7,166,368 | B2 | 1/2007 | Lecloux et al. |
| 7,276,617 | B2 | 10/2007 | Sotoyama et al. |
| 8,106,199 | B2 | 1/2012 | Jabbour et al. |
| 8,389,725 | B2 | 3/2013 | Li et al. |
| 8,669,364 | B2 | 3/2014 | Li et al. |
| 8,846,940 | B2 | 9/2014 | Li et al. |
| 9,076,974 | B2 | 7/2015 | Li et al. |
| 9,082,989 | B2 | 7/2015 | Li et al. |
| 9,203,039 | B2 | 12/2015 | Li et al. |
| 2002/0189666 | A1 | 12/2002 | Forrest et al. |
| 2006/0093854 | A1 | 5/2006 | Sotoyama et al. |
| 2006/0094875 | A1 | 5/2006 | Itoh et al. |
| 2007/0111025 | A1 | 5/2007 | Lennartz et al. |
| 2007/0224447 | A1 | 9/2007 | Sotoyama et al. |
| 2008/0067925 | A1 | 3/2008 | Oshiyama et al. |
| 2008/0269491 | A1 | 10/2008 | Jabbour et al. |
| 2009/0278453 | A1* | 11/2009 | Yam .......... H01L 51/0091 313/504 |
| 2011/0028723 | A1 | 2/2011 | Li et al. |
| 2011/0062429 | A1* | 3/2011 | Kai .......... C07D 487/04 257/40 |
| 2011/0301351 | A1 | 12/2011 | Li et al. |
| 2012/0205554 | A1 | 8/2012 | Hollis et al. |
| 2013/0137870 | A1 | 5/2013 | Li et al. |
| 2013/0168656 | A1* | 7/2013 | Tsai .......... C07F 15/0086 257/40 |
| 2013/0237706 | A1* | 9/2013 | Li .......... C07D 213/643 546/4 |
| 2014/0084261 | A1* | 3/2014 | Brooks .......... C07F 15/0086 257/40 |
| 2014/0249310 | A1 | 9/2014 | Li et al. |
| 2015/0018558 | A1 | 1/2015 | Li et al. |
| 2015/0105556 | A1* | 4/2015 | Li .......... C09K 11/06 546/4 |
| 2015/0311456 | A1 | 10/2015 | Li et al. |
| 2016/0028028 | A1* | 1/2016 | Li .......... H01L 51/0087 548/103 |
| 2016/0043331 | A1* | 2/2016 | Li .......... H01L 51/0087 546/4 |

FOREIGN PATENT DOCUMENTS

| | | |
|---|---|---|
| JP | 2008069268 A | 3/2010 |
| WO | WO0070655 A3 | 5/2004 |
| WO | WO2004039781 A9 | 6/2005 |
| WO | WO2005075600 A1 | 8/2005 |
| WO | WO2005103195 A1 | 11/2005 |
| WO | WO2005105746 A1 | 11/2005 |
| WO | WO2006082742 A1 | 8/2006 |
| WO | WO2006100888 A1 | 9/2006 |
| WO | WO2009086209 A3 | 10/2009 |
| WO | WO2009111299 A3 | 12/2009 |
| WO | WO2011136755 * | 11/2011 |

OTHER PUBLICATIONS

Sumby; Organometallics, 2003, 22, 2358-2360.*
Nonoyama; Polyhedron 1985, 4, 765-768.*
Wu; Angew. Chem. Int. Ed. 2000, 39, 3933-3935.*
Song; Organometallics 2001, 20, 4683-4689.*
Seward; Inorg. Chem., 2004, 43 , 978-985.*
Dorwald; "Side Reactions in Organic Synthesis: A Guide to Successful Synthesis Design" 2005 Wiley-VCH Verlag GmbH & Co. KGaA, Wienheim, chapter 1.*
Lisa Murphy et al., "Blue-shifting the monomer and excimer phosphorescence of tridentate cyclometallated platinum(II) complexes for optimal white-light OLEDs," Chem. Commun. 48(47), Jun. 14, 2012, pp. 5817-5819.
Yun Chi et al., "Transition-metal phosphors with cyclometalating ligands: fundamentals and applications," Chemical Society Reviews 39(2), Feb. 2010, pp. 638-655.
Eric Turner et al., "Cyclometalated Platinum Complexes with Luminescent Quantum Yields Approaching 100%," Inorganic Chemistry 52, Jun. 2013, pp. 7344-7351.
Guijie Li et al., "Efficient and Stable White Organic Light-Emitting Diodes Employing a Single Emitter," Advanced Materials 26, 2014, pp. 2931-2936.
Xiaohui Yang et al., "Efficient Blue- and White-Emitting Electrophosphorescent Devices Based on Platinum(II) [1,3-Difluoro-4,6-di(2-pyridinyl)benzene] Chloride," Advanced Materials 20, 2008, pp. 2405-2409.
Tyler Fleetham et al., "Efficient deep blue electrophosphorescent devices based on platinum(II) bis(n-methyl-imidazolyl)benzene chloride," Organic Electronics 13, 2012, pp. 1430-1435.
Bei-Ping Yan et al., "Efficient White Organic Light-Emitting Devices Based on Phosphorescent Platinum(II)/Fluorescent Dual-Emitting Layers," Advanced Materials 19, 2007, pp. 3599-3603.
Zixing Wang et al., "Facile Synthesis and Characterization of Phosphorescent Pt(N N∧C∧N C N∧C∧N N)X Complexes," Inorganic Chemistry 49(24), 2010, pp. 11276-11286.
Tyler Fleetham et al., "Single-Doped White Organic Light-Emitting Device with an External Quantum Efficiency Over 20%," Advanced Materials 25, 2013 pp. 2573-2576.
Xiao-Chun Hang et al., "Highly Efficient Blue-Emitting Cyclometalated Platinum(II) Complexes by Judicious Molecular Design," Angew. Chem. Int. Ed. 52, 2013, pp. 6753-6756.
Jan Kalinowski et al., "Light-emitting devices based on organometallic platinum complexes as emitters," Coordination Chemistry Reviews 255, 2011, pp. 2401-2425.
Kai Li et al., "Light-emitting platinum(II) complexes supported by tetradentate dianionic bis(N-heterocyclic carbene) ligands: towards robust blue electrophosphors," Chemical Science 4, 2013 pp. 2630-2644.
Lixin Xiao et al., "Recent Progresses on Materials for Electrophosphorescent Organic Light-Emitting Devices," Advanced Materials 23, 2011, pp. 926-952.
Le Zhao et al., "Luminescent Amphiphilic 2,6-Bis(1-alkylpyrazol-3-yl)pyridyl Platinum(II) Complexes: Synthesis, Characterization, Electrochemical, Photophysical, and Langmuir-Blodgett Film Formation Studies," Chemistry A European Journal 16, 2010, pp. 6797-6809.
Nathan Bakken et al., "Highly efficient white organic light-emitting device using a single emitter," Journal of Photonics for Energy 2, 2012, pp. 021203-1-021203-7.
J.A. GarethWilliams et al., "Optimising the luminescence of platinum(II) complexes and their application in organic light emitting devices (OLEDs)," Coordination Chemistry Reviews 252, 2008, pp. 2596-2611.
Valery N. Kozhevnikov et al., "Phosphorescent, Terdentate, Liquid-Crystalline Complexes of Platinum(II): Stimulus-Dependent Emission," Angew. Chem. Int. Ed. 47, 2008, pp. 6286-6289.
Steven C. F. Kui et al., "Robust Phosphorescent Platinum(II) Complexes Containing Tetradentate ONCN Ligands: Excimeric Excited State and Application in Organic White-Light-Emitting Diodes," Chemistry A European Journal 19, 2013, pp. 69-73.
Mai-Yan Yuen et al., "Synthesis, Photophysical and Electrophosphorescent Properties of Fluorene-Based Platinum(II) Complexes," Chemistry A European Journal 16 2010, pp. 14131-14141.

(56) References Cited

OTHER PUBLICATIONS

Xiaohui Yang et al., "Highly efficient excimer-based white phosphorescent devices with improved power efficiency and color rendering index," Applied Physics Letters 93, 2008, pp. 193305-1-193305-3.

S. A. Willison et al., "A Luminescent Platinum(II) 2,6-Bis(N-pyrazolyl)pyridine Complex", Inorg. Chem. vol. 43, pp. 2548-2555, 2004.

J. M. Longmire et al., "Synthesis and X-ray Crystal Structures of Palladium(II) and Platinum(II) Complexes of the PCP-Type Chiral Tridentate Ligand", Organometallics, vol. 17, pp. 4374-4379, 1998.

V. Adamovich et al., "High efficiency single dopant white electrophosphorescent light emitting diodes", New J. Chem, vol. 26, pp. 1171-1178. 2002.

Del Cano et al., "Near-infrared electroluminescence based on perylenediimide-doped tris(8-quinolinolato) aluminum", Applied Physics Letters, 88, pp. 071117-1-071117-3, 2006.

B. Harrison et al., "Near-infrared electroluminescence from conjugated polymer/lanthanide porphyrin blends", Applied Physics Letter, vol. 79, No. 23, pp. 3770-3772, Dec. 3, 2001.

J. Kido et al., "Organo Lanthanide Metal Complexes for Electroluminescent Materials", Chem. Rev., vol. 102, pp. 2357-2368, 2002.

S. Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.

S. Lamansky et al., "Synthesis and Characterization of Phosphorescent Cyclometalated Iridium Complexes", Inorg. Chem., vol. 40, pp. 1704-1711, 2001.

X. Li et al, "Synthesis and properties of novel poly(p-phenylenevinylene) copolymers for near-infrared emitting diodes", European Polymer Journal, vol. 41, pp. 2923-2933, 2005.

P. Peumans et al., "Small molecular weight organic thin-film photodetectors and solar cells", Journal of Applied Physics, vol. 93, No. 7, pp. 3693-3723, Apr. 1, 2003.

Rand et al., Organic Double-Heterostructure Photovoltaic Cells Employing Thick Tris (acetylacetonato) ruthenium (III) Exciton-Blocking Layers, Advanced Materials vol. 17, pp. 2714-2718, 2005.

C.W. Tang, "Two-layer organic photovoltaic cell", Appl. Phys. Letters 48 (2), pp. 183-185, 1986).

Vanhelmont et al., "Synthesis, Crystal Structure, High-Resolution Optical Spectroscopy, and Extended Huckel Calculations for [Re(CO)4(thpy)] (thpy- 2-(2-Thienyl)pyridinate). Comparison with Related Cyclometalated Complexes", Inorg. Chem., vol. 36, pp. 5512-5517, 1997.

Williams et al., "Organic light-emitting diodes having exclusive near-infrared electrophosphorescence", Applied Physics Letters, vol. 89, pp. 083506 (3 pages), 2006.

Forrest et al., "Measuring the Efficiency of Organic Light-Emitting Devices", Advanced Materials, vol. 15, No. 13, pp. 1043-1048, 2003.

Cardenas et al., "Divergent Behavior of Palladium(II) and Platinum(II) in the Metalation of 1,2-Di(2-pyridyl) benzene," Organometallics 1999, 18, pp. 3337-3341.

Williams et al., "An Alternative Route to Highly Luminescent Platinum(II) Complexes," Inorg. Chem., 2003, 42, pp. 8609-8611.

Sanna et al., "Platinum complexes with N—N—C ligands. Synthesis, electrochemical and spectroscopic characteristics of platinum(II) and relevant electroreduced species," Inorganica Chimica Acta 305, 2000, pp. 189-205.

Ionkin, A.S. et al.: Synthesis and structural characterization of a series of novel polyaromatic ligands containing pyrene and related biscyclometalated iridium complexes. Organometallics, vol. 25, pp. 1461-1471, 2006.

Develay et al. "Cyclometalated Platinum(II) Complexes of Pyrazole-Based, N N∧C∧N C N∧C∧N N-Coordinating, Terdentate Ligands: the Contrasting Influence of Pyrazolyl and Pyridyl Rings on Luminescence" Inorganic Chemistry, vol. 47, No. 23, 2008, pp. 11129-11142.

* cited by examiner

TRIDENTATE CYCLOMETALATED METAL COMPLEXES WITH SIX-MEMBERED COORDINATION RINGS

CROSS-REFERENCE TO RELATED APPLICATION

This application claims priority to U.S. Ser. No. 62/029,737 entitled "TRIDENTATE CYCLOMETALATED METAL COMPLEXES WITH SIX-MEMBERED COORDINATION RINGS" and filed on Jul. 28, 2014, which is incorporated by reference herein in its entirety.

TECHNICAL FIELD

This disclosure relates to tridentate cyclometalated metal complexes with six-membered coordination rings.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, and devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to metal complexes suitable for use as emitters in organic light emitting diodes (OLEDs), display, and lighting applications.

Disclosed herein are complexes of General Formula I:

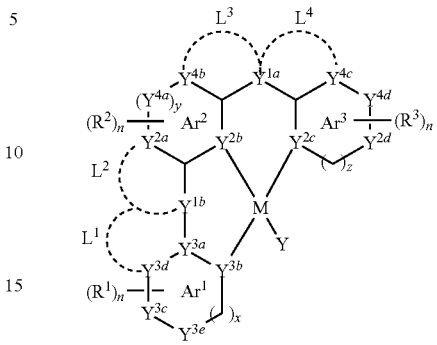

General Formula I wherein:
M is Pt(II), Pd(II), Ir(I), Rh(I), or Au(II),
x=0 or 1, and when x=0, $Y^{3e}$ is directly linked to $Y^{3b}$;
y=0 or 1, and when y=0, $Y^{2a}$ is directly linked to $Y^{4b}$;
z=0 or 1, and when m=0, $Y^2$ is directly linked to $Y^{2d}$;
each of $Ar^1$, $Ar^2$, and $Ar^3$ independently represents five-membered heteroaryl or six-membered aryl or heteroaryl,
each n is independently an integer of 1 to 4, valency permitting,
each $R^1$, $R^2$, and $R^3$ is independently hydrogen, halogen, hydroxyl, amino, nitro, thiol, or substituted or unsubstituted alkyl, alkoxyl, alkenyl, alkynyl, heteroaryl, or aryl, and any two of $R^1$, any two of $R^2$, and any two of $R^3$ are optionally linked together,
$Y^{1a}$ is O, S, $NR^{2a}$, C, $CR^{2a}$, $CR^{2b}R^{2c}$, $PR^{2a}$, $AsR^{2a}$, $BR^{2a}$, or $SiR^{2d}R^{2e}$, where each of $R^{2a}$, $R^{2b}$, $R^{2c}$, $R^{2d}$, and $R^{2e}$ is independently hydrogen, halogen, or substituted or unsubstituted alkyl, alkenyl, alkynyl, or aryl;
$Y^{1b}$ is O, S, $NR^{3a}$, C, $CR^{3a}$, $CR^{3b}R^{3c}$, $PR^{2a}$, $AsR^{2a}$, $BR^{2a}$, $P(O)R^{2a}$, $As(O)R^{2a}$, or $SiR^{3d}R^{3e}$, where each of $R^{3a}$, $R^{3b}$, $R^{3c}$, $R^{3d}$, and $R^{3e}$ is independently hydrogen, halogen, or substituted or unsubstituted alkyl, alkenyl, alkynyl, or aryl,
each of $Y^{2a}$ and $Y^{2d}$ is independently C, N, $NR^{4a}$, or $CR^{4b}$, where each of $R^{4a}$ and $R^{4b}$ is independently hydrogen, hydroxyl, amino, nitro, thiol, or substituted or unsubstituted $C_1$-$C_4$ alkyl, alkoxy, or aryl;
each of $Y^{2b}$ and $Y^{2c}$ is independently C or N,
each of $Y^{3a}$, $Y^{3b}$, $Y^{3c}$, $Y^{3d}$ and $Y^{3e}$ is independently C, N, O, S, $NR^{5a}$, $PR^{5b}$, $AsR^{5c}$, $SiR^{5d}R^{5e}$, $BR^{5f}$, or $CR^{5g}$, where each of $R^{5a}$, $R^{5b}$, $R^{5c}$, $R^{5d}$, $R^{5e}$, $R^{5f}$, and $R^{5g}$ is independently hydrogen or substituted or unsubstituted $C_1$-$C_4$ alkyl or aryl; or $ZR^{6a}R^{6b}$; Z is C or Si; and each of $R^{6a}$ and $R^{6b}$ is independently substituted or unsubstituted $C_1$-$C_4$ alkyl or aryl,
each of $Y^{4a}$, $Y^{4b}$, $Y^{4c}$, and $Y^{4d}$ is independently N, $NR^{4e}$, C, or $CR^{4f}$, where each of $R^{4e}$ and $R^{4f}$ is independently hydrogen, hydroxyl, amino, nitro, thiol, or substituted or unsubstituted $C_1$-$C_4$ alkyl, alkoxy, or aryl,
each of $L^1$, $L^2$, $L^3$, and $L^4$ is independently present or absent, and if present, each independently represents a substituted or unsubstituted five-membered heteroaryl, six-membered aryl, six-membered heteroaryl, or any fused combination thereof, and
Y is halogen, $OCOR^{7a}$, $OR^{7b}$, $SR^{7c}$, $NR^{7d}$, $R^{7e}$, CO, $NR^{7f}$, $PR^{7g}$, $AsR^{7h}$, $R^{7i}R^{7j}$, $C=CR^{7k}$, substituted or unsubstituted: pyridine, imidazole, pyrazole, oxazole, thiazole, isoxazole, or quinoline, where each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, and $R^{7k}$ is independently acetylacetonate, pyridine, imidazole; substituted or unsubstituted: alkyl, alkenyl, alkynyl, aryl, or trisubstituted phosphine.

Examples of General Formula I include Formulas 1-5 below:

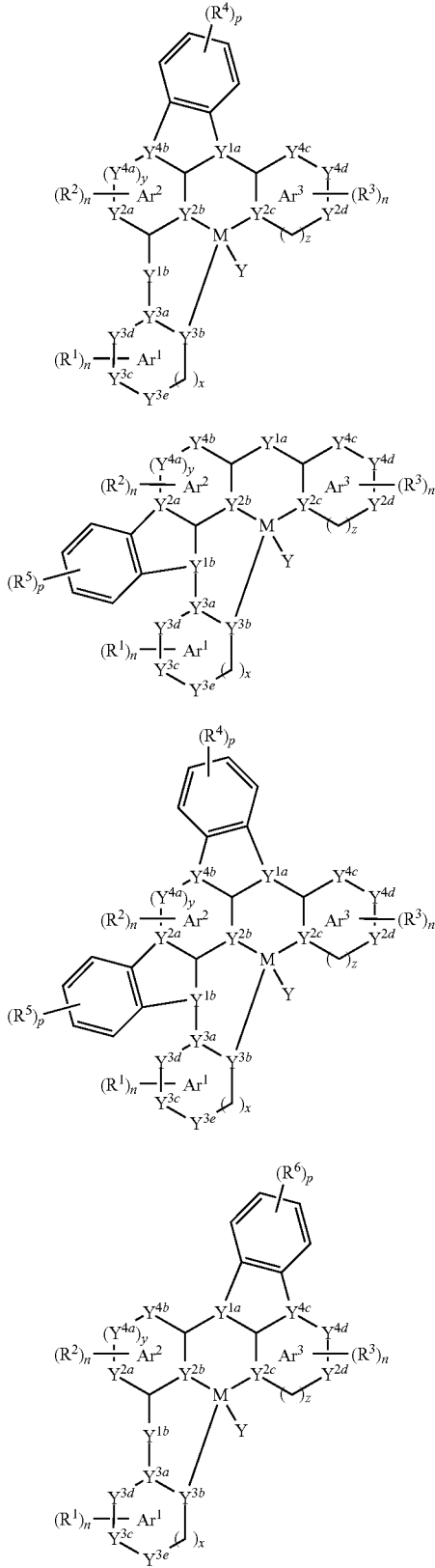

Formula 1

Formula 2

Formula 3

Formula 4

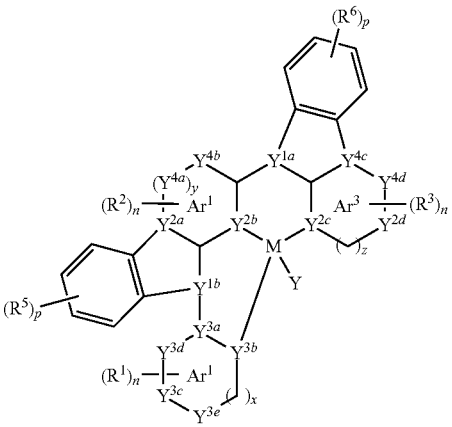

Formula 5

In Formula 1, $L^3$ is present and p is 4. Each $R^4$ is independently hydrogen, halogen, hydroxyl, amino, nitro, thiol, or substituted or unsubstituted alkyl, alkoxyl, alkenyl, alkynyl, heteroaryl, or aryl, and any two of $R^4$ are optionally linked together.

In Formula 2, $L^2$ is present and p is 4. Each $R^5$ is independently hydrogen, halogen, hydroxyl, amino, nitro, thiol, or substituted or unsubstituted alkyl, alkoxyl, alkenyl, alkynyl, heteroaryl, or aryl, and any two of $R^5$ are optionally linked together.

In Formula 3, $L^2$ and $L^3$ are present and p is 4. Each $R^4$ and $R^5$ is independently hydrogen, halogen, hydroxyl, amino, nitro, thiol, or substituted or unsubstituted alkyl, alkoxyl, alkenyl, alkynyl, heteroaryl, or aryl; any two of $R^4$ are optionally linked together, and any two of $R^5$ are optionally linked together.

In Formula 4, $L^4$ is present and p is 4. Each $R^6$ is independently hydrogen, halogen, hydroxyl, amino, nitro, thiol, or substituted or unsubstituted alkyl, alkoxyl, alkenyl, alkynyl, heteroaryl, or aryl, and any two of $R^6$ are optionally linked together.

In Formula 5, $L^2$ and $L^4$ are present and p is 4. Each $R^5$ and $R^6$ is independently hydrogen, halogen, hydroxyl, amino, nitro, thiol, or substituted or unsubstituted alkyl, alkoxyl, alkenyl, alkynyl, heteroaryl, or aryl; any two of $R^5$ are optionally linked together, and any two of $R^6$ are optionally linked together.

Also disclosed herein are compositions including one or more complexes disclosed herein.

Also disclosed herein are devices, such as OLEDs, including one or more complexes or compositions disclosed herein.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

Figure 1:
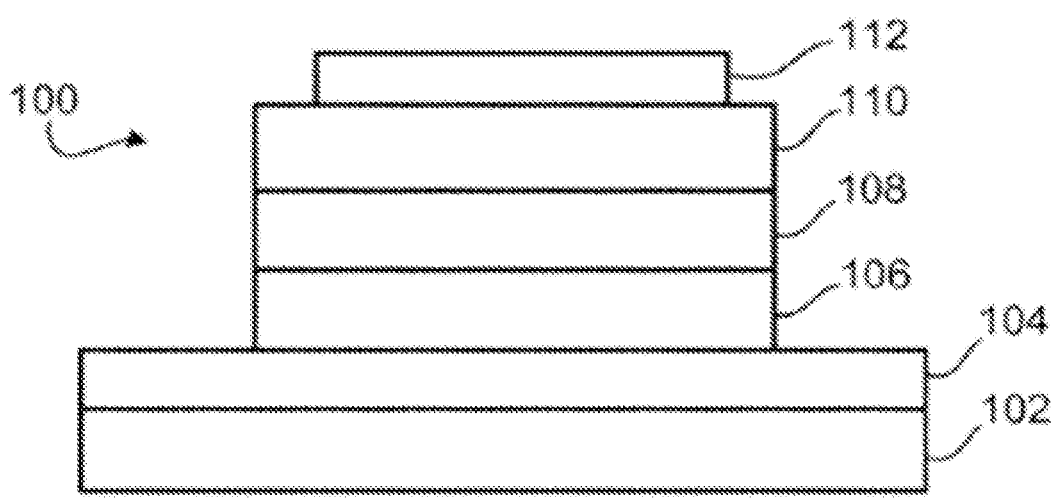
FIG. 1 depicts a cross-sectional view of an exemplary organic light-emitting diode (OLED).

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of compounds of the present disclosure, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods described herein.

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH (COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

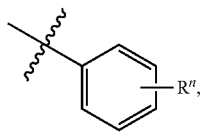

which is understood to be equivalent to a formula:

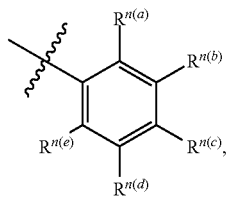

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs) and a great deal of attention has been received both in the academic and industrial fields. And much achievement has been made in the past decade to lead to the lucrative commercialization of the technology, for example, OLEDs have been used in advanced displays in smart phones, televisions and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state ($T_1$) energy of the blue phosphors is high, which generally means that the lowest triplet excited state ($T_1$) energy of host materials for the blue devices should be even higher. This leads to difficulty in the development of the host materials for the blue devices.

This disclosure provides a materials design route by introducing a carbon group (C, Si, Ge) bridging to the ligand of the metal complexes. As described herein, it was found that the photoluminescence spectrum of the carbon bridging Pt complex had a significant blue shift comparing to the nitrogen bridging one with the same emissive group. It was also found that chemical structures of the emissive luminophores and the ligands could be modified, and also the metal could be changed to adjust the singlet states energy and the triplet states energy of the metal complexes, which all could affect the optical properties of the complexes.

The metal complexes described herein can be tailored or tuned to a specific application that requires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can generally exhibit different optical properties, including emission and absorption spectra. The color of the metal complexes can be tuned by modifying the conjugated groups on the fluorescent luminophores and ligands.

The emission of such complexes can be tuned, for example, from the ultraviolet to near-infrared, by, for example, modifying the ligand or fluorescent luminophore structure. A fluorescent luminophore is a group of atoms in an organic molecule that can absorb energy to generate singlet excited state(s). The singlet exciton(s) produce(s) decay rapidly to yield prompt luminescence. In one aspect, the complexes can provide emission over a majority of the visible spectrum. In a specific example, the complexes described herein can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, emitters in organic light emitting diodes (OLEDs), or a combination thereof. In another aspect, the inventive complexes can be useful in light emitting devices, such as, for example, compact fluorescent lamps (CFL), light emitting diodes (LEDs), incandescent lamps, and combinations thereof.

Disclosed herein are compounds or compound complexes comprising platinum, palladium, iridium, rhodium, and gold. The terms "compound," "complex," and "compound complex" are used interchangeably herein. In one aspect, the compounds disclosed herein have a neutral charge.

The compounds disclosed herein exhibit desirable properties and have emission and/or absorption spectra that can be tuned via the selection of appropriate ligands. The compounds disclosed herein include delayed fluorescent emitters, phosphorescent emitters, or a combination thereof. In one aspect, the compounds disclosed herein are delayed fluorescent emitters. In another aspect, the compounds disclosed herein are phosphorescent emitters. In yet another aspect, a compound disclosed herein is both a delayed fluorescent emitter and a phosphorescent emitter. In another aspect, any one or more of the compounds, structures, or portions thereof, specifically recited herein, can be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency and/or operational lifetimes in lighting devices, such as, for example, organic light emitting devices, as compared to conventional materials.

Compounds described herein can be made using a variety of methods, including, but not limited to those recited in the examples.

The compounds disclosed herein include delayed fluorescent emitters, phosphorescent emitters, or a combination thereof. In one aspect, the compounds disclosed herein are delayed fluorescent emitters. In another aspect, the compounds disclosed herein are phosphorescent emitters. In yet another aspect, a compound disclosed herein is both a delayed fluorescent emitter and a phosphorescent emitter.

Tridentate cyclometalated complexes with 6-membered coordination rings represented by General Formula I are efficient emitters having tunable emission wavelengths in the visible range. These compounds have a high quantum efficiency of emission, which is proportional to the integral of the wavefunction of the ground state and the excited state, and favors a small difference in equilibrium geometry between the ground state and the excited state.

Disclosed herein are complexes of General Formula I:

General Formula I

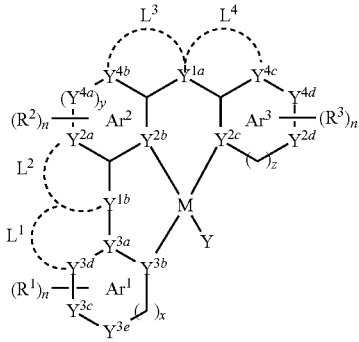

wherein:
M is Pt(II), Pd(II), Ir(I), Rh(I), or Au(II),
x=0 or 1, and when x=0, $Y^{3e}$ is directly linked to $Y^{3b}$
y=0 or 1, and when y=0, $Y^{2a}$ is directly linked to $Y^{4b}$;
z=0 or 1, and when m=0, $Y^{2c}$ is directly linked to $Y^{2d}$;

each of $Ar^1$, $Ar^2$, and $Ar^3$ independently represents five-membered heteroaryl or six-membered aryl or heteroaryl;
each n is independently an integer of 1 to 4, valency permitting;
each $R^1$, $R^2$, and $R^3$ is independently hydrogen, halogen, hydroxyl, amino, nitro, thiol, or substituted or unsubstituted alkyl, alkoxyl, alkenyl, alkynyl, heteroaryl, or aryl, and any two of $R^1$, any two of $R^2$, and any two of $R^3$ are optionally linked together;
$Y^{1a}$ is O, S, $NR^{2a}$, C, $CR^{2a}$, $CR^{2b}R^{2c}$, $PR^{2a}$, $AsR^{2a}$, $BR^{2a}$, or $SiR^{2d}R^{2e}$, where each of $R^{2a}$, $R^{2b}$, $R^{2c}$, $R^{2d}$, and $R^{2e}$ is independently hydrogen, halogen, or substituted or unsubstituted alkyl, alkenyl, alkynyl, or aryl;
$Y^{1b}$ is O, S, $NR^{3a}$, C, $CR^{3a}$, $CR^{3b}R^{3c}$, $PR^{2a}$, $AsR^{2a}$, $BR^{2a}$, $P(O)R^{2a}$, $As(O)R^{2a}$, or $SiR^{3d}R^{3e}$ where each of $R^{3a}$, $R^{3b}$, $R^{3c}$, $R^{3d}$, and $R^{3e}$ is independently hydrogen, halogen, or substituted or unsubstituted alkyl, alkenyl, alkynyl, or aryl;
each of $Y^{2a}$ and $Y^{2d}$ is independently C, N, $NR^{4a}$, or $CR^{4b}$, where each of $R^{4a}$ and $R^{4b}$ is independently hydrogen, hydroxyl, amino, nitro, thiol, or substituted or unsubstituted $C_1$-$C_4$ alkyl, alkoxy, or aryl;
each of $Y^{2b}$ and $Y^{2c}$ is independently C or N;
each of $Y^{3a}$, $Y^{3b}$, $Y^{3c}$, $Y^{3d}$ and $Y^{3e}$ is independently C, N, O, S, $NR^{5a}$, $PR^{5b}$, $AsR^{5c}$, $SiR^{5d}R^{5e}$, $BR^{5f}$, or $CR^{5g}$, where each of $R^{5a}$, $R^{5b}$, $R^{5c}$, $R^{5d}$, $R^{5e}$, $R^{5f}$, and $R^{5g}$ is independently hydrogen or substituted or unsubstituted $C_1$-$C_4$ alkyl or aryl; or $ZR^{6a}R^{6b}$; Z is C or Si; and each of $R^{6a}$ and $R^{6b}$ is independently substituted or unsubstituted $C_1$-$C_4$ alkyl or aryl;
each of $Y^{4a}$, $Y^{4b}$, $Y^{4c}$, and $Y^{4d}$ is independently N, $NR^{4e}$, C, or $CR^{4f}$, where each of $R^{4e}$ and $R^{4f}$ is independently hydrogen, hydroxyl, amino, nitro, thiol, or substituted or unsubstituted $C_1$-$C_4$ alkyl, alkoxy, or aryl;
each of L, $L^2$, $L^3$, and $L^4$ is independently present or absent, and if present, each independently represents a substituted or unsubstituted five-membered heteroaryl, six-membered aryl, six-membered heteroaryl, or any fused combination thereof, and
Y is halogen, $OCOR^{7a}$, $OR^{7b}$, $SR^{7c}$, $NR^{7d}R^{7e}$, CO, $NR^{7f}$, $PR^{7g}$, $AsR^{7h}R^{7i}R^{7j}$, C≡$CR^{7k}$, or substituted or unsubstituted pyridine, imidazole, pyrazole, oxazole, thiazole, isoxazole, or quinoline, where each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, and $R^{7k}$ is independently acetylacetonate, pyridine, imidazole; substituted or unsubstituted: alkyl, alkenyl, alkynyl, aryl, or trisubstituted phosphine.

Examples of General Formula I include Formulas 1-5 below:

Formula 1

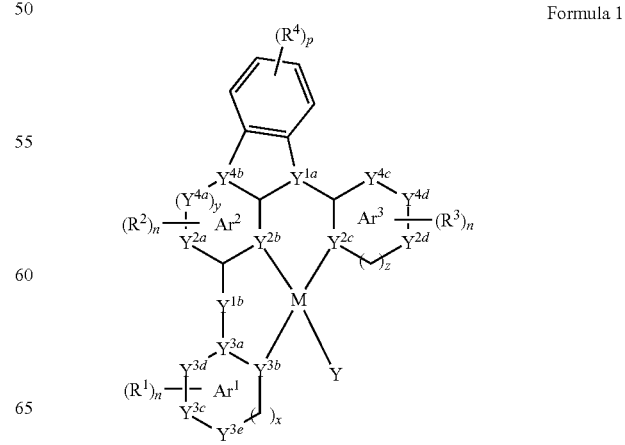

-continued

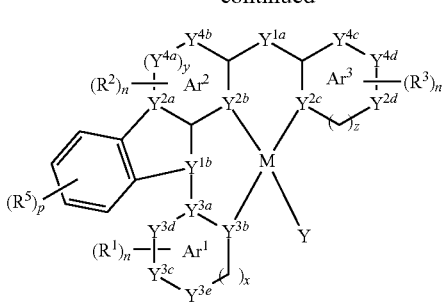

Formula 2

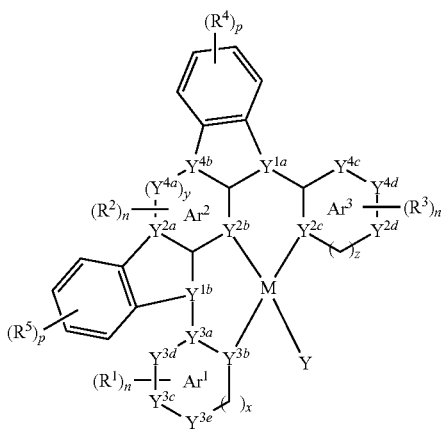

Formula 3

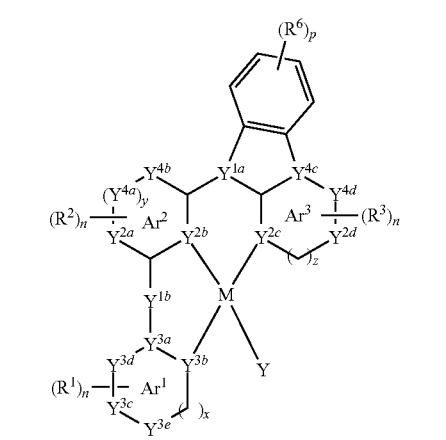

Formula 4

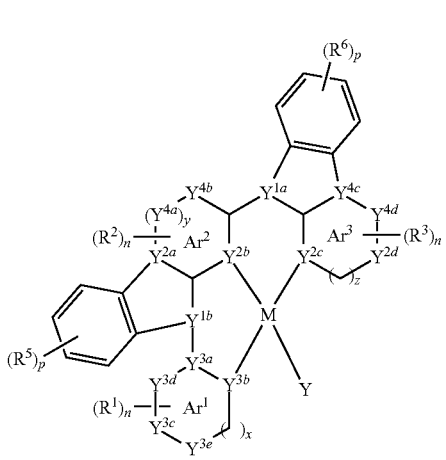

Formula 5

In Formula 1, $L^3$ is present and p is 4. Each $R^4$ is independently hydrogen, halogen, hydroxyl, amino, nitro, thiol, or substituted or unsubstituted alkyl, alkoxyl, alkenyl, alkynyl, heteroaryl, or aryl, and any two of $R^4$ are optionally linked together.

In Formula 2, $L^2$ is present and p is 4. Each $R^5$ is independently hydrogen, halogen, hydroxyl, amino, nitro, thiol, or substituted or unsubstituted alkyl, alkoxyl, alkenyl, alkynyl, heteroaryl, or aryl, and any two of $R^5$ are optionally linked together.

In Formula 3, $L^2$ and $L^3$ are present and p is 4. Each $R^4$ and $R^5$ is independently hydrogen, halogen, hydroxyl, amino, nitro, thiol, or substituted or unsubstituted alkyl, alkoxyl, alkenyl, alkynyl, heteroaryl, or aryl; any two of $R^4$ are optionally linked together, and any two of $R^5$ are optionally linked together.

In Formula 4, $L^4$ is present and p is 4. Each $R^6$ is independently hydrogen, halogen, hydroxyl, amino, nitro, thiol, or substituted or unsubstituted alkyl, alkoxyl, alkenyl, alkynyl, heteroaryl, or aryl, and any two of $R^6$ are optionally linked together.

In Formula 5, $L^2$ and $L^4$ are present and p is 4. Each $R^5$ and $R^6$ is independently hydrogen, halogen, hydroxyl, amino, nitro, thiol, or substituted or unsubstituted alkyl, alkoxyl, alkenyl, alkynyl, heteroaryl, or aryl; any two of $R^5$ are optionally linked together, and any two of $R^6$ are optionally linked together.

Tridentate cyclometalated compounds of General Formula I include at least one 6-membered coordination ring, and have a rigid molecular geometry. As such, these compounds are efficient emitters. The emission wavelengths of complexes of General Formula I may be tuned the visible range by selection of metal, ring size, substituents, and other parameters in General Formula I. This class of emitters is suitable for full color displays and lighting applications.

Other examples of tridentate cyclometalated complexes with 6-membered coordination rings represented by General Formula I are shown below.

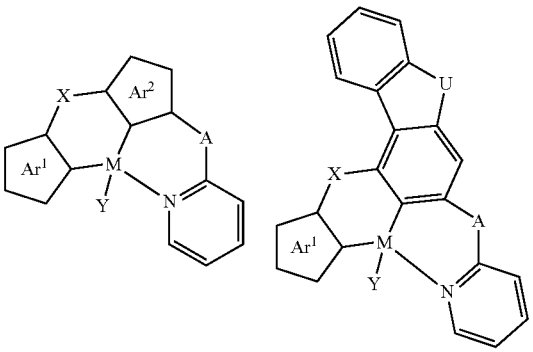

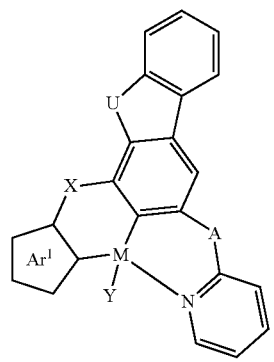

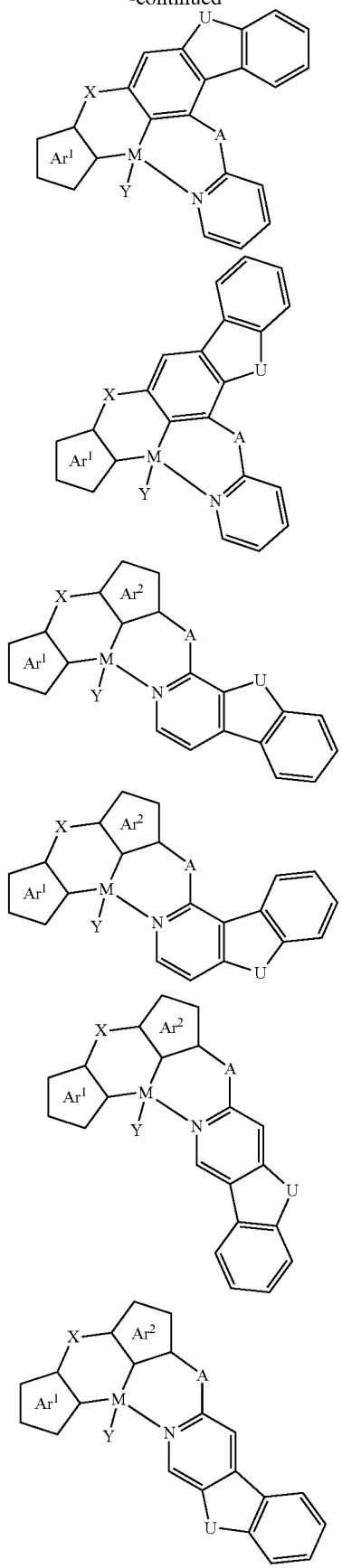
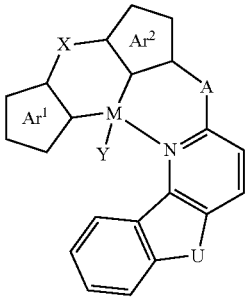
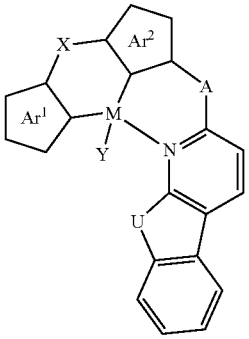
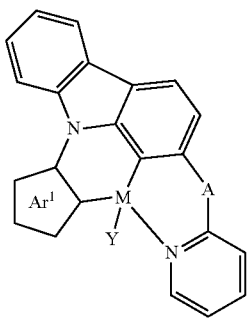
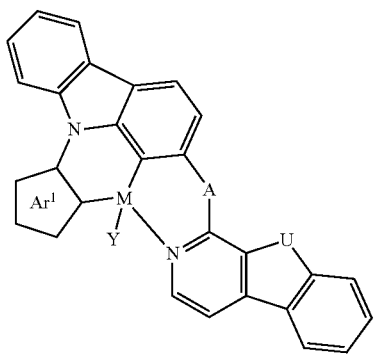
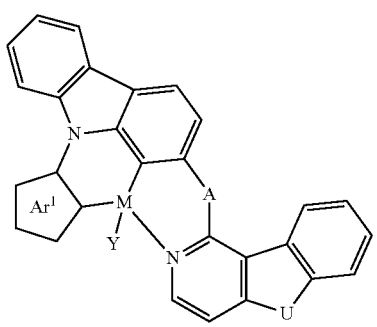

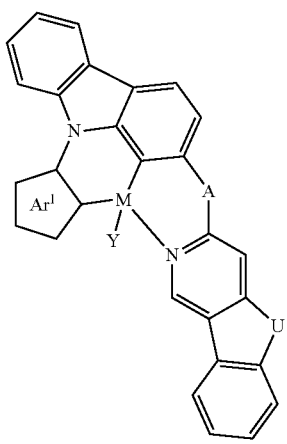
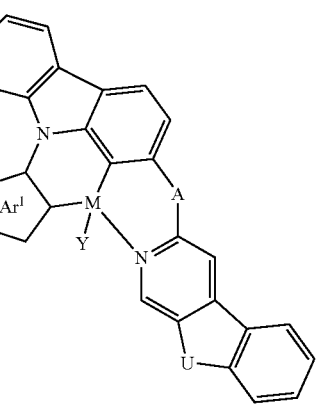
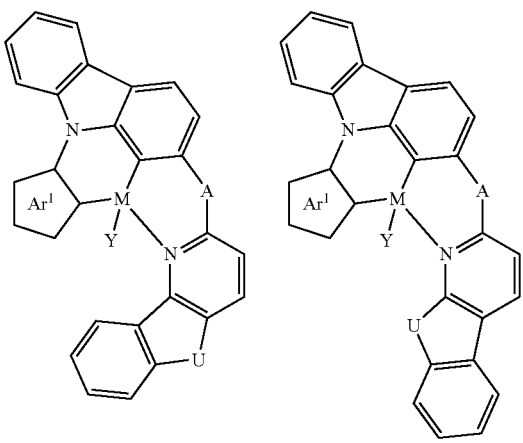
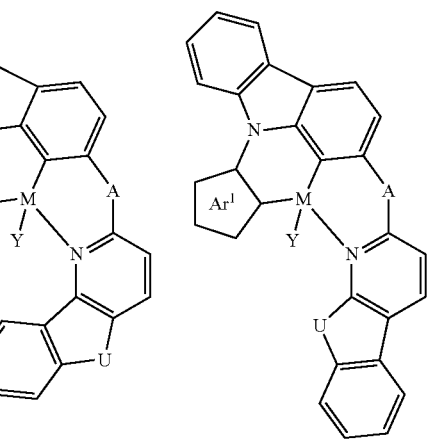
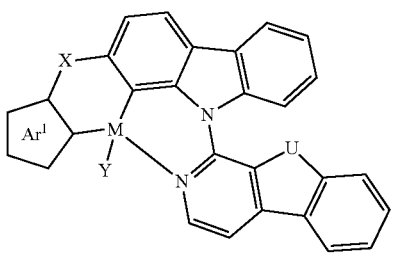
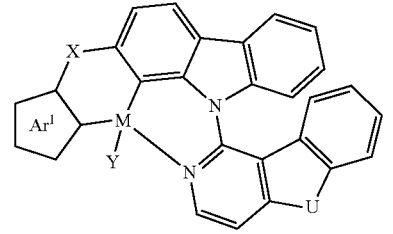
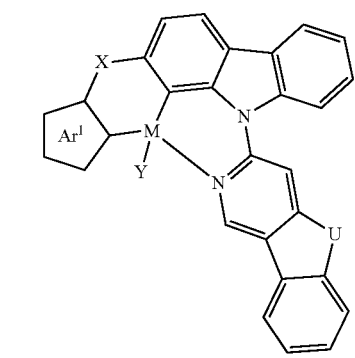
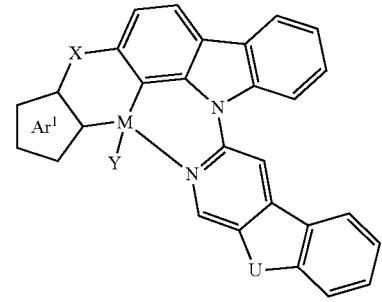
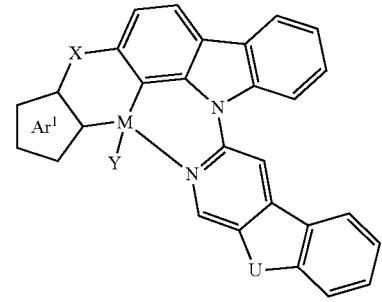
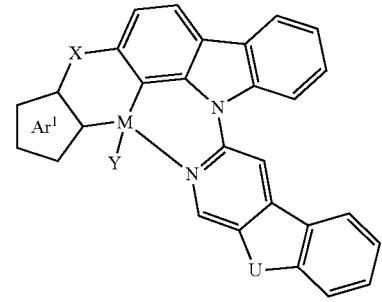
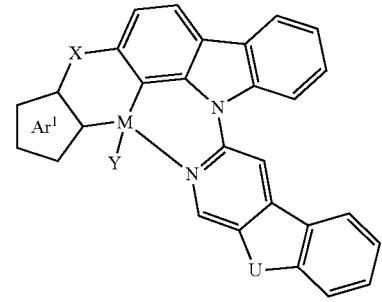

-continued
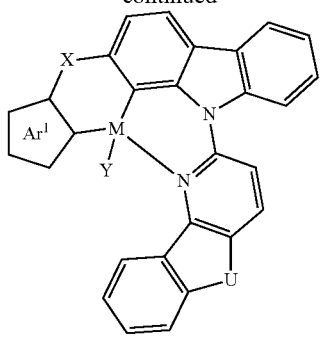
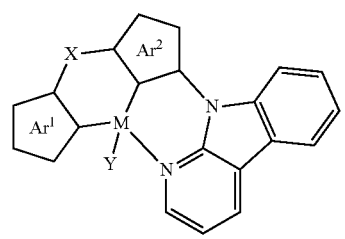
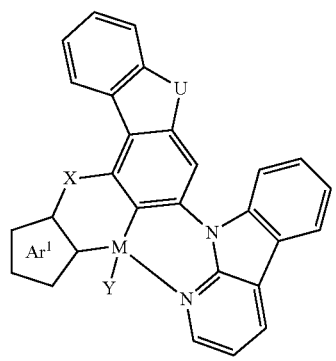
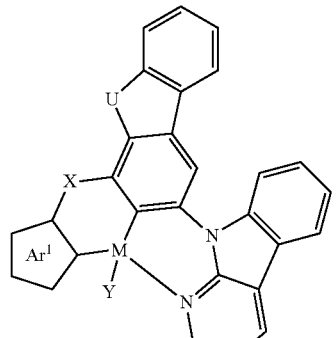
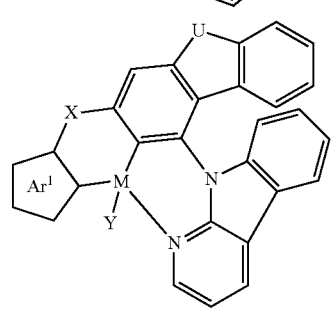
-continued
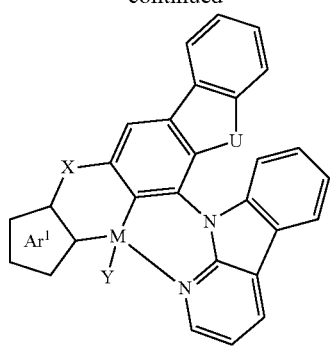
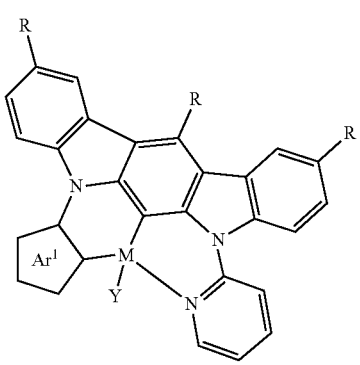
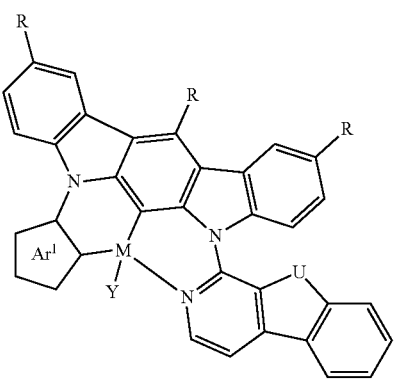
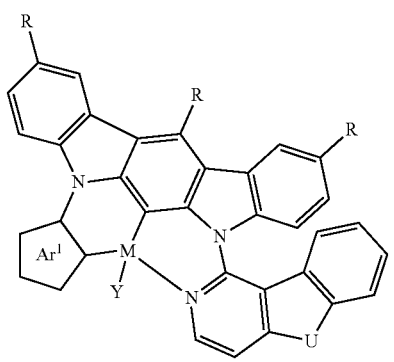

-continued
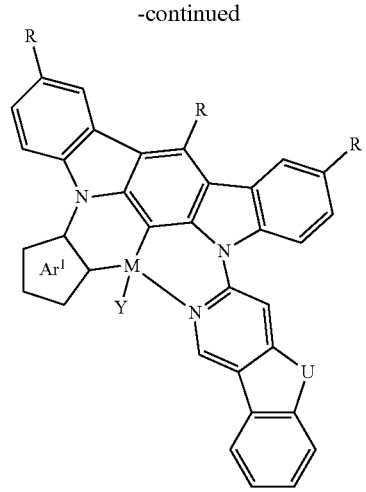
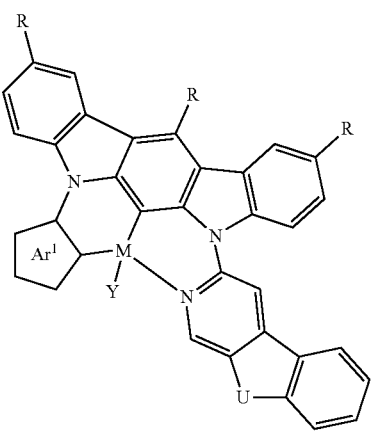
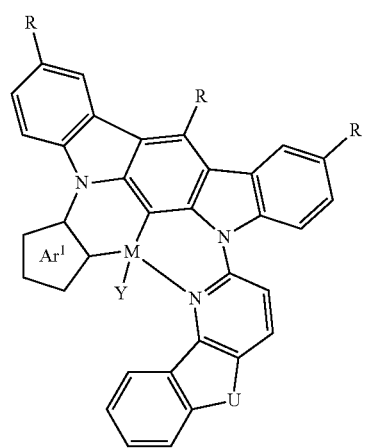
-continued
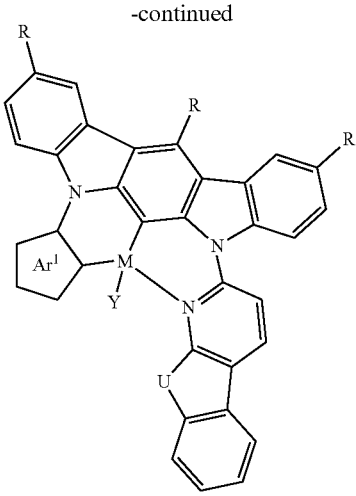
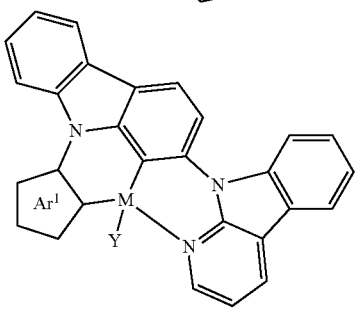
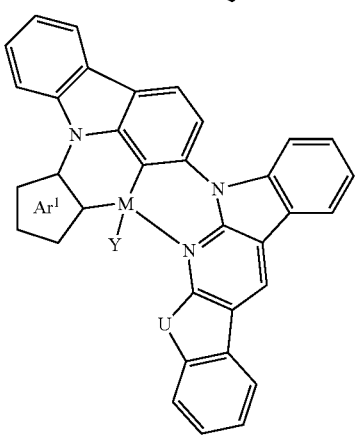
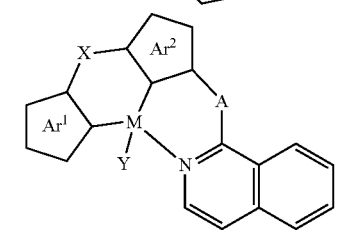
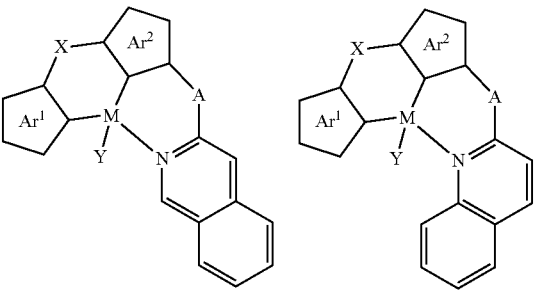

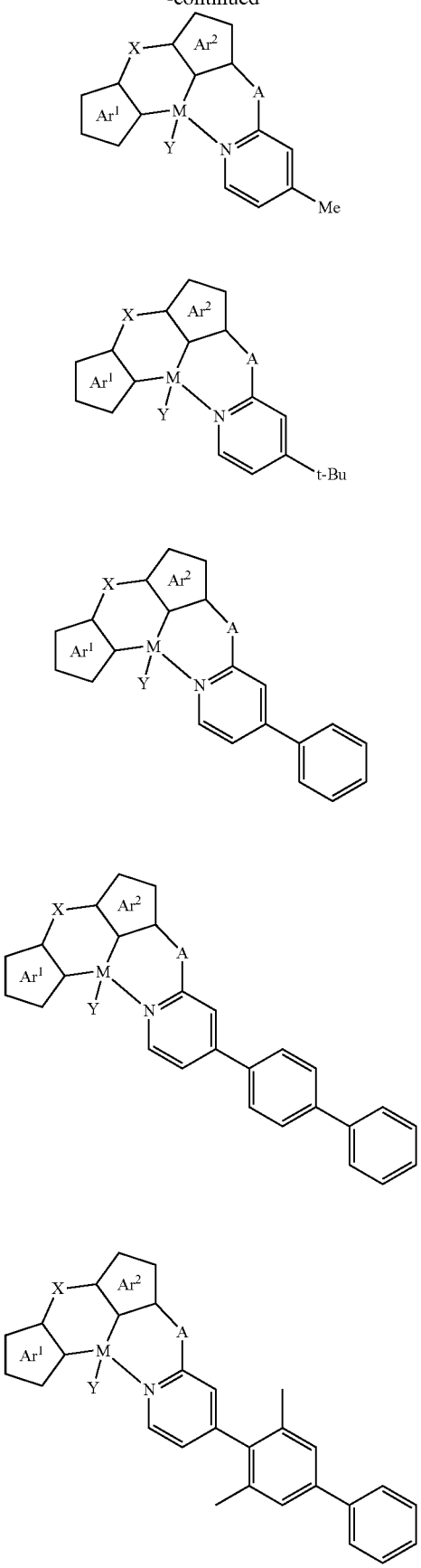
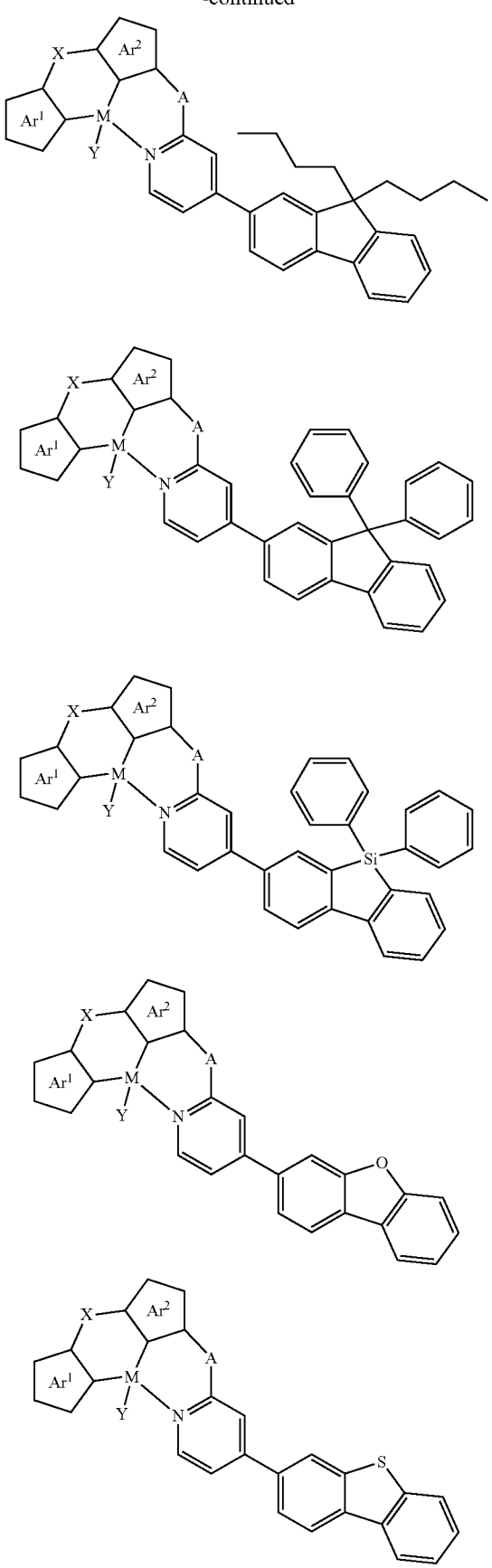

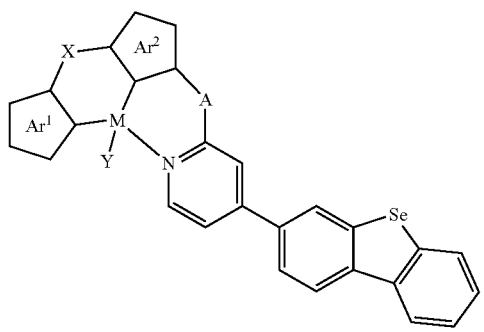
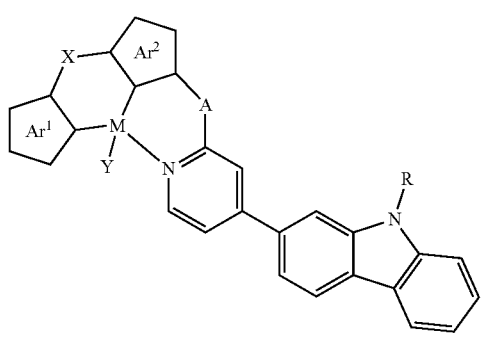
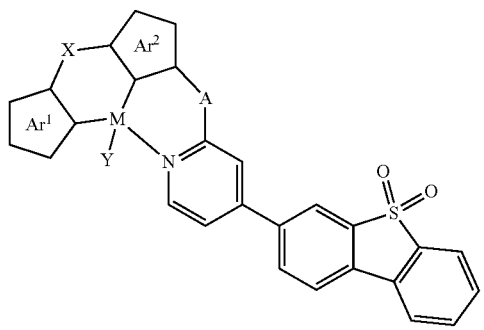
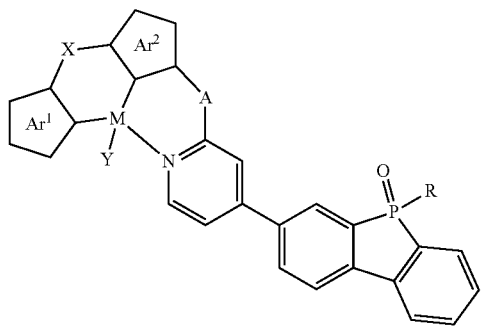
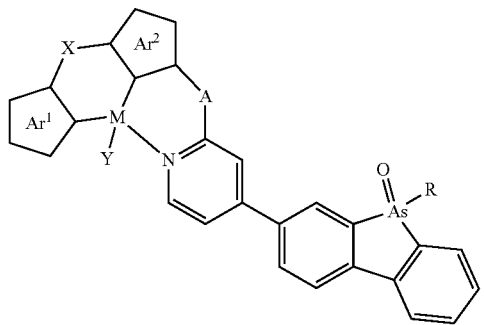
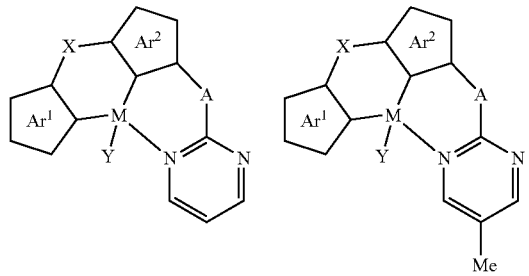
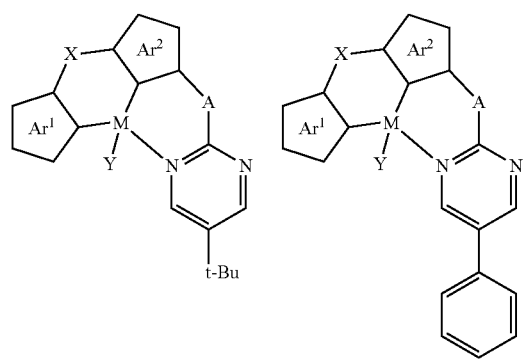
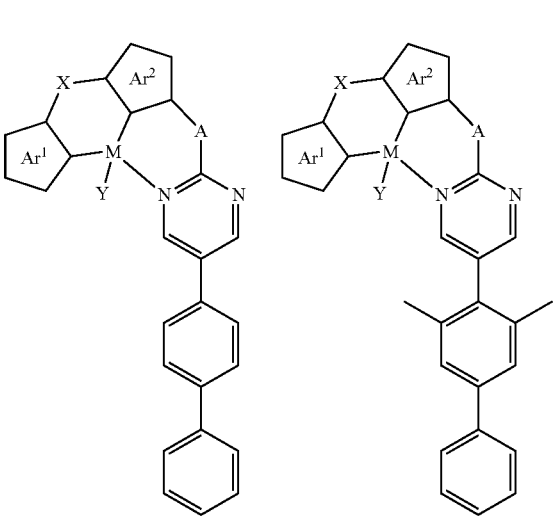
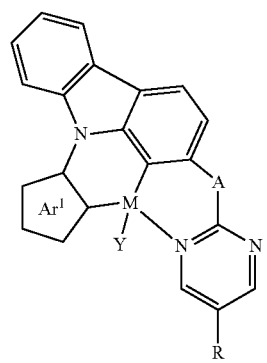

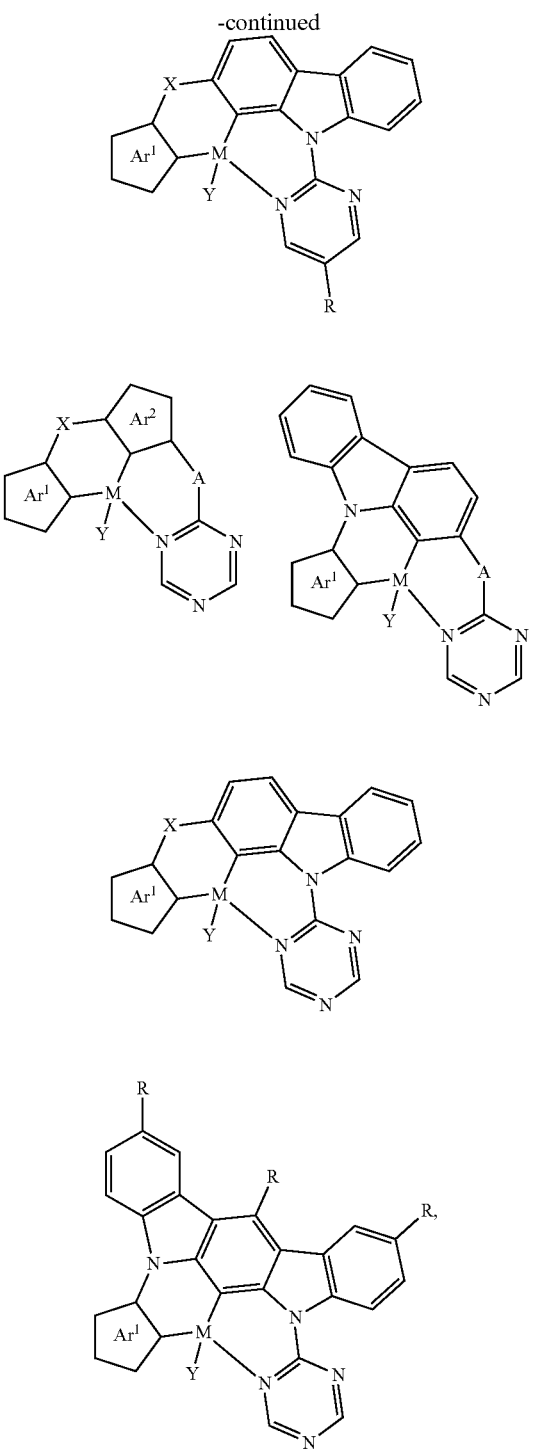

When

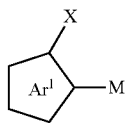

is one of

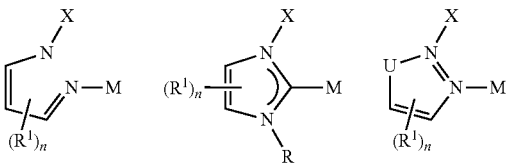

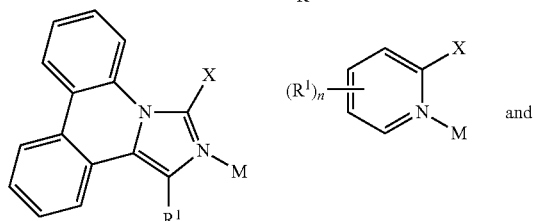

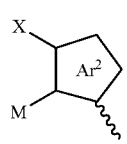

is one of

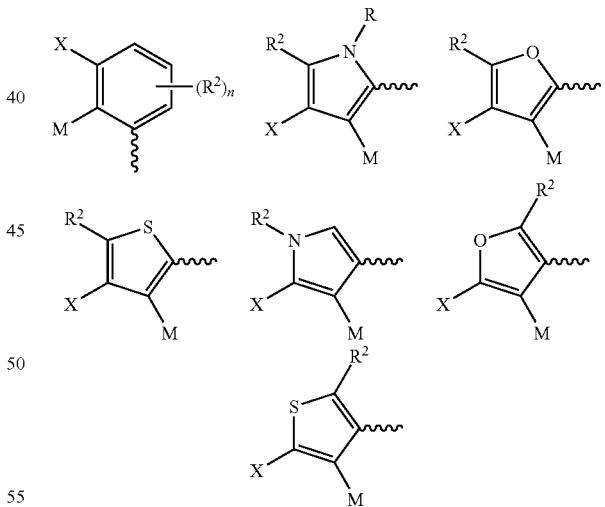

then

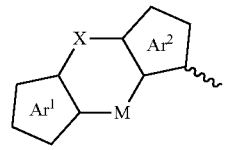

wherein:
X is O, S, NR, PR, AsR, CR$_2$, SiR$_2$, or BR.
A is O, S, NR, PR, AsR, CR$_2$, SiR$_2$, or BR.
U is O, S, NR, PR, AsR, CR$_2$, SiR$_2$, or BR.
M is Pt(II) or Pd(II),
each R is independently hydrogen, halogen, substituted or unsubstituted: alkyl, alkenyl, alkynyl, and aryl, and
each of Ar$^1$ and Ar$^2$ independently represents substituted or unsubstituted five-membered heteroaryl or six-membered aryl or heteroaryl.

includes, but is not limited to, the following
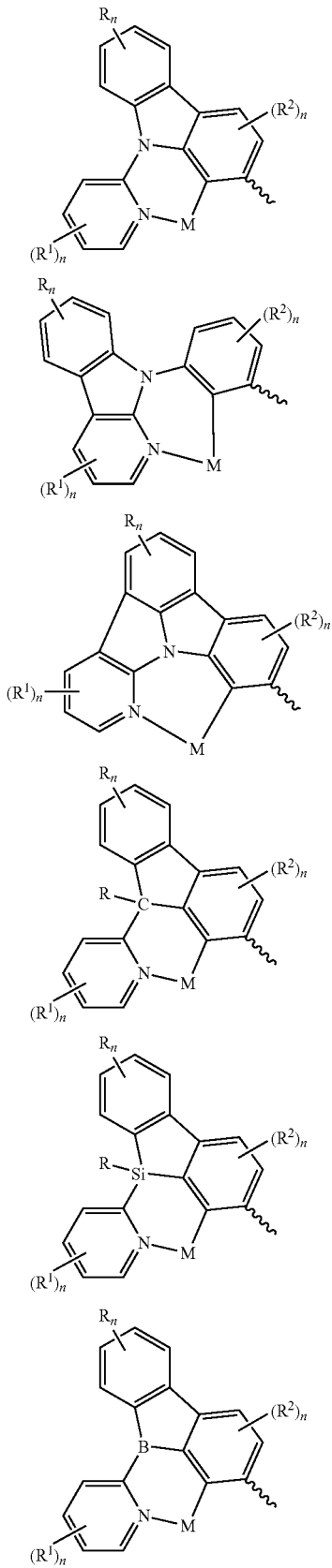
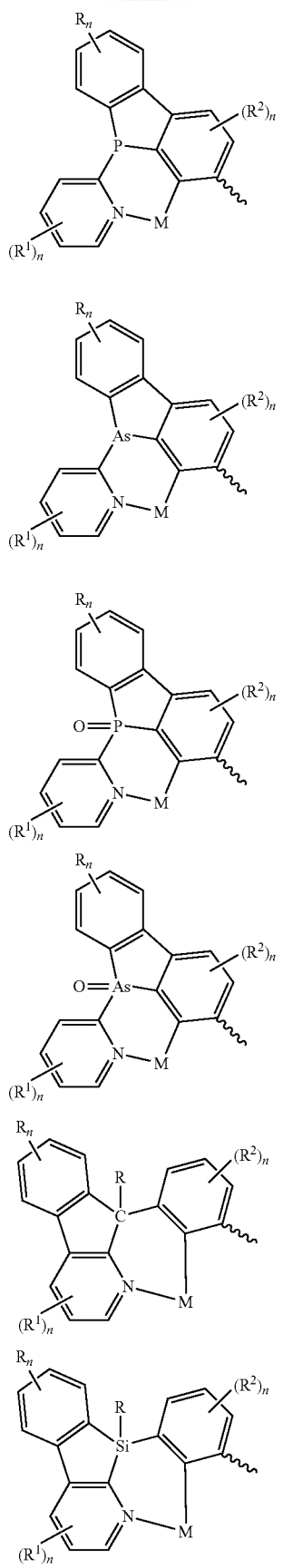

-continued
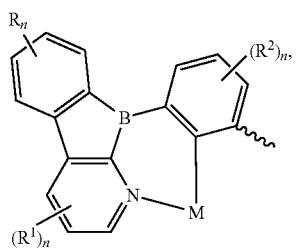
Y is Cl, Br, I, OR, OCOR, SR, NRR, or C≡CR, and
each R is independently hydrogen, halogen, substituted or unsubstituted: alkyl, alkenyl, alkynyl, or aryl.
When
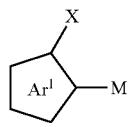
is one of
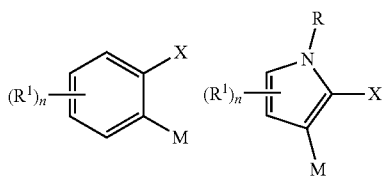
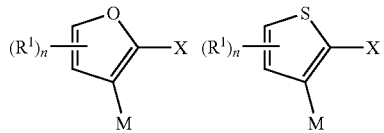
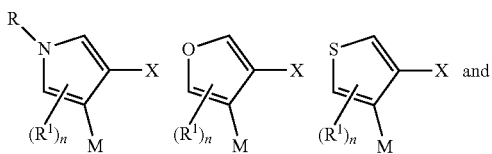 and
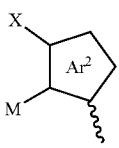
is one of
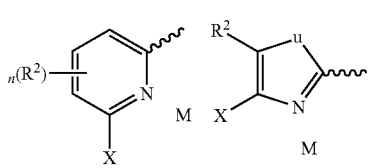
-continued
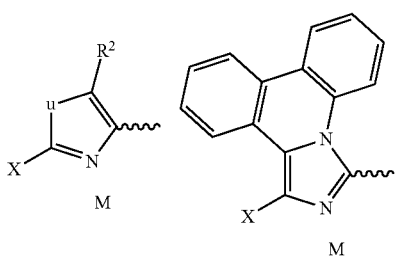
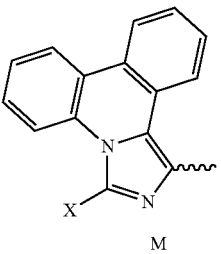
then
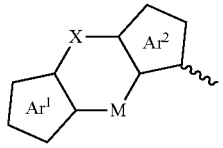
includes, but is not limited to, the following
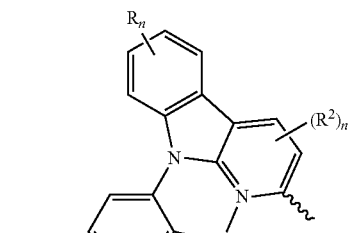
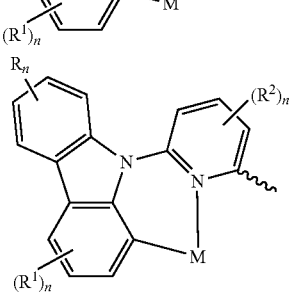
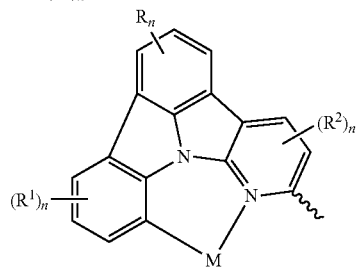

-continued
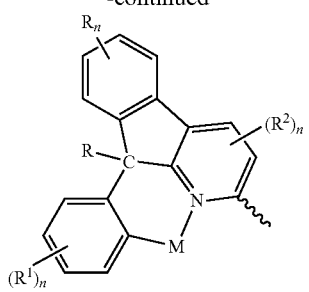
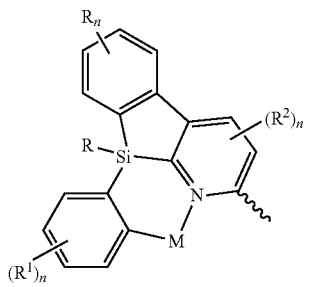
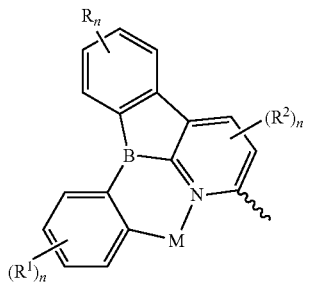
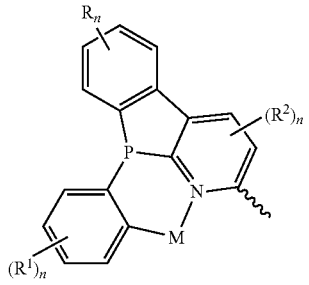
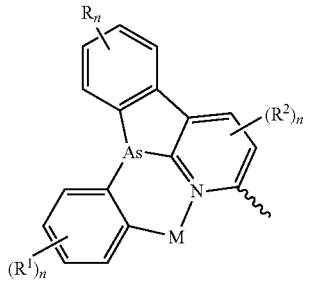
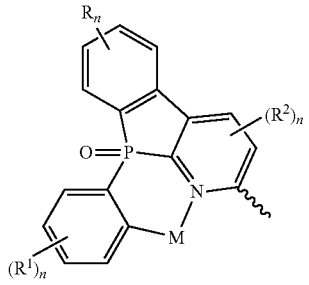
-continued
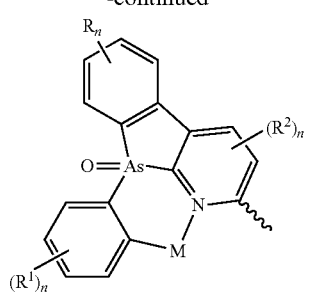
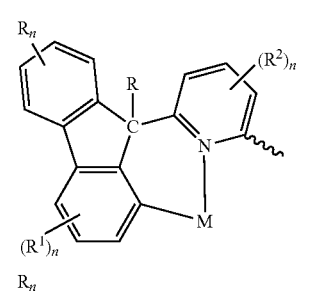
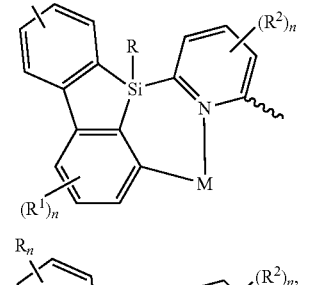
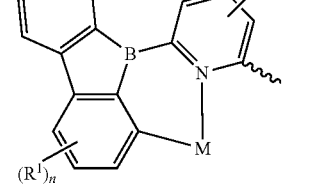
Y is Cl, Br, I, OR, OCOR, SR, NRR, or C≡CR, and each R and R' is independently hydrogen, halogen, substituted or unsubstituted: alkyl, alkenyl, alkynyl, or aryl.
When
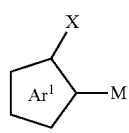
is one of
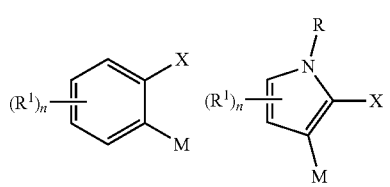

-continued
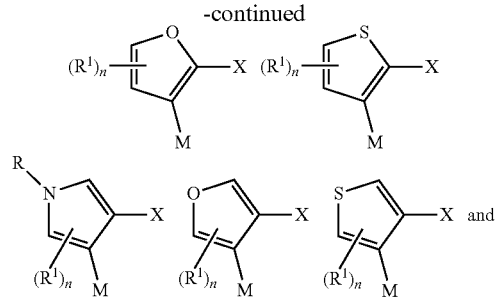
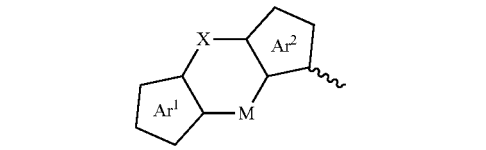
is one of
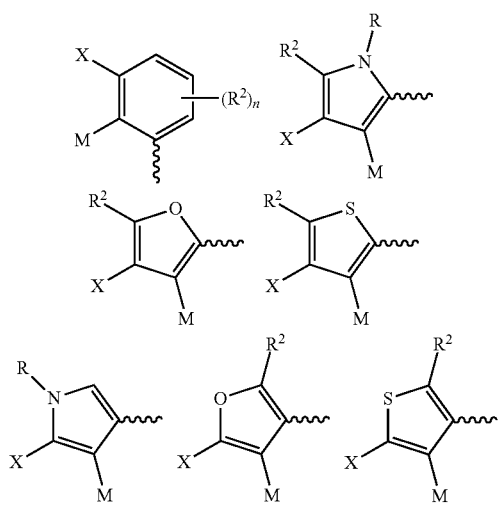
then
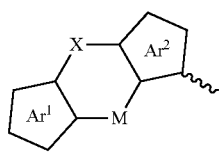
includes, but is not limited to, the following
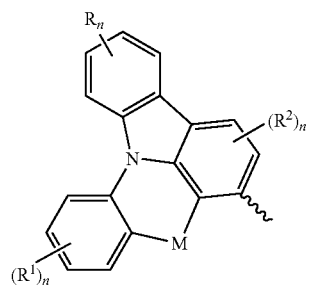
-continued
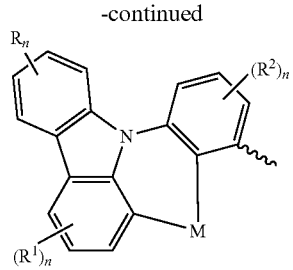
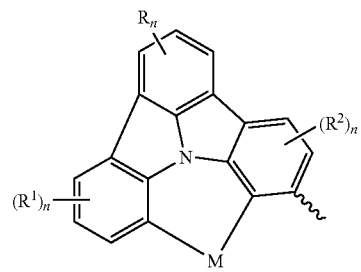
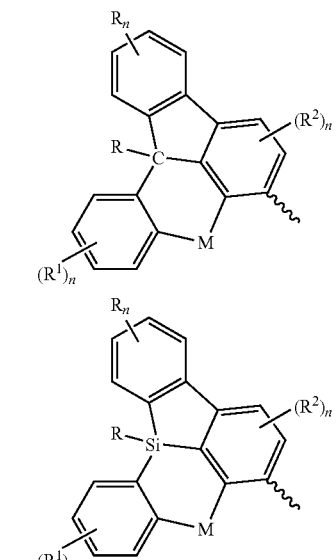
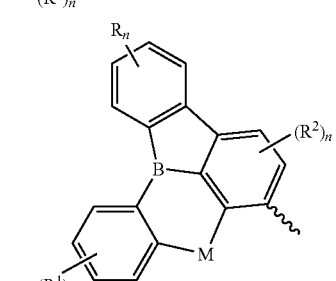
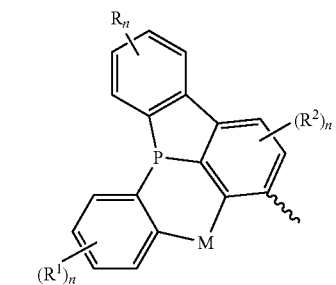

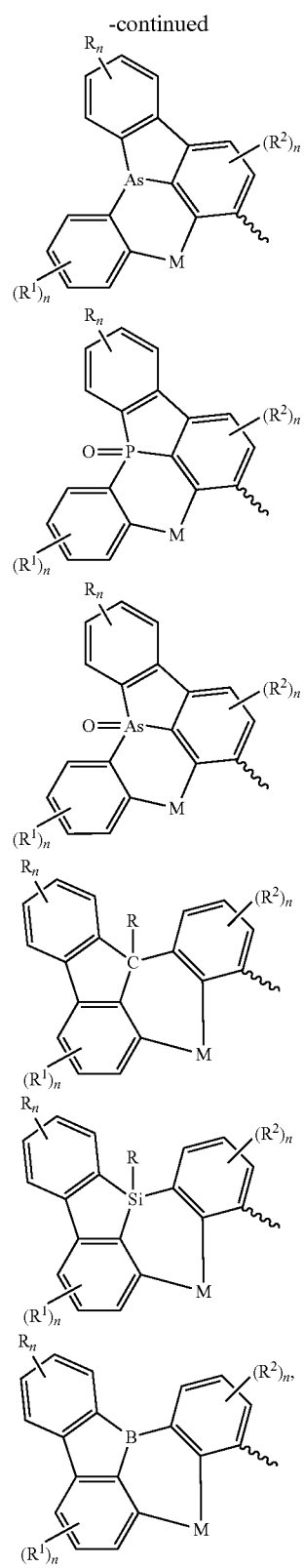
Y is CO, NR$_3$, PR$_3$, AsR$_3$, substituted or unsubstituted: pyridine, imidazole, pyrazole, oxazole, thiazole, isoxazole, and
each R is independently hydrogen, substituted or unsubstituted: alkyl, alkenyl, alkynyl, or aryl.
In one aspect, the complex of General Formula I has one of the following structures:
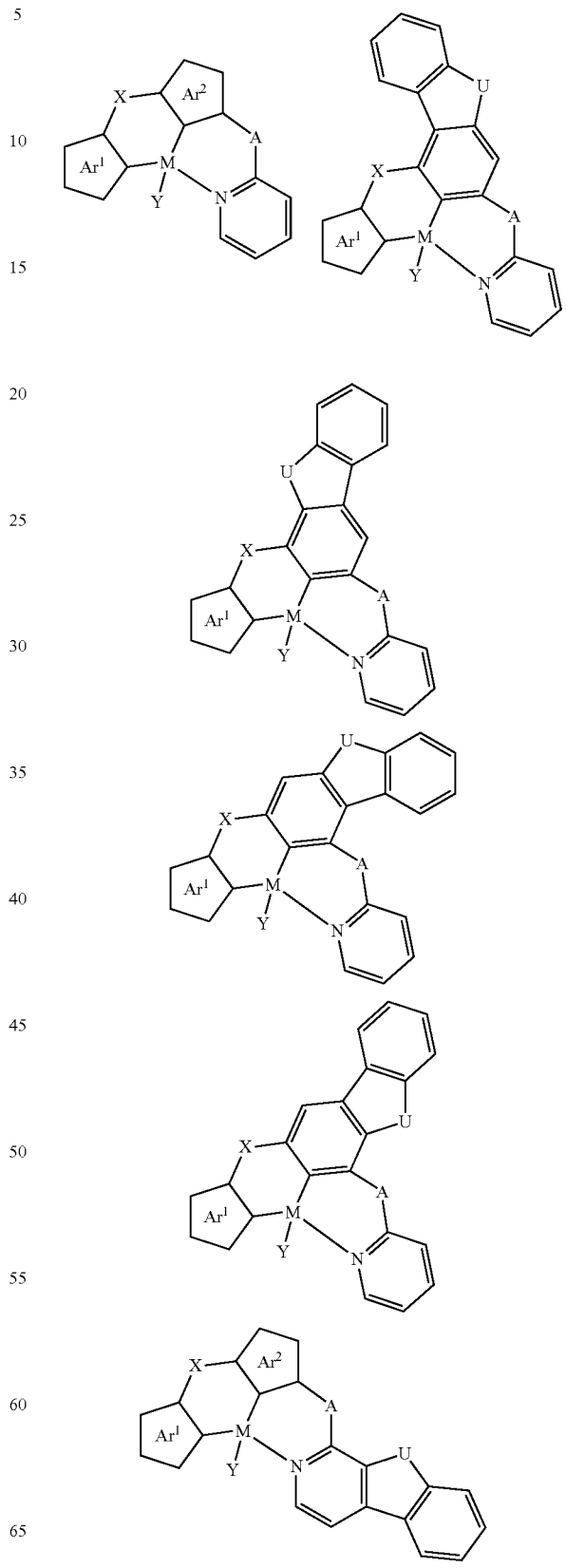

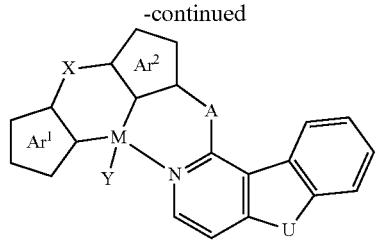
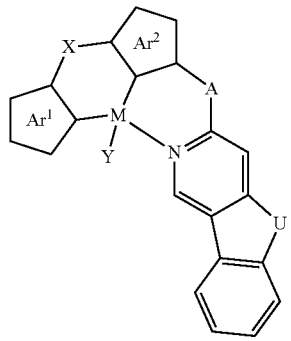
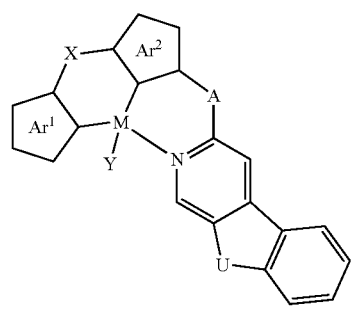
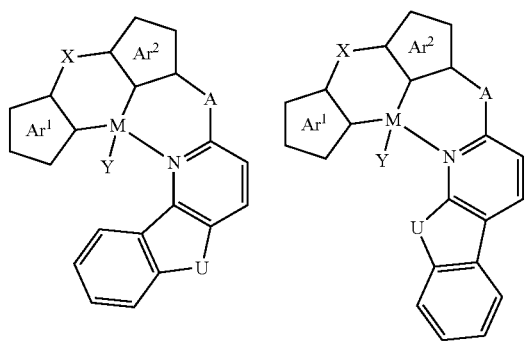
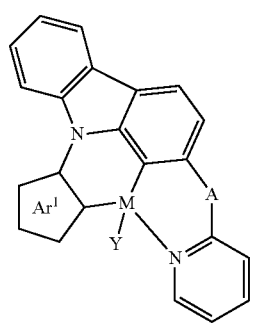
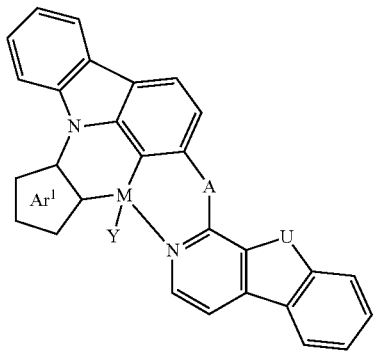
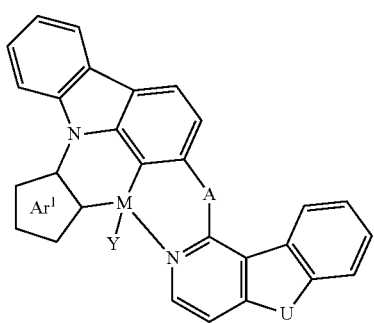
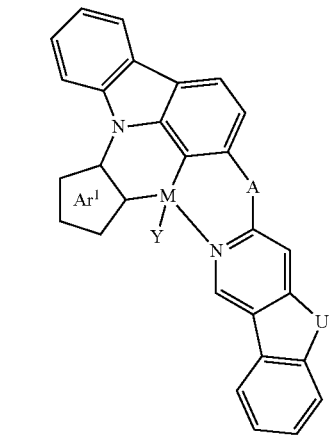
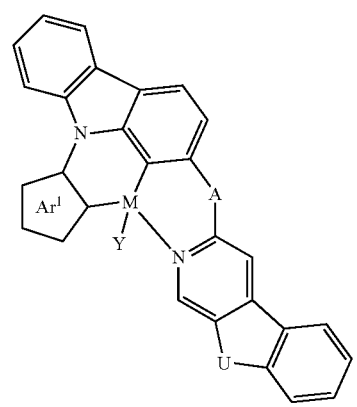

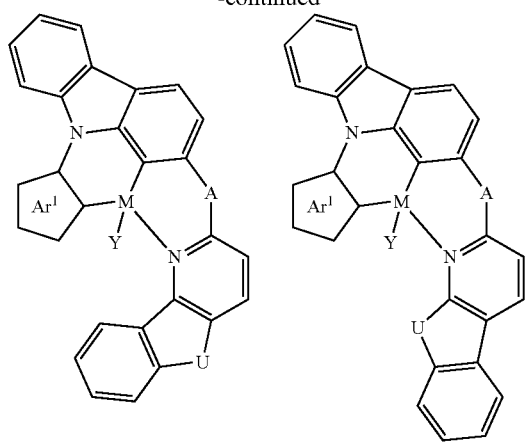
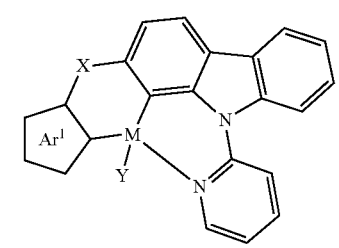
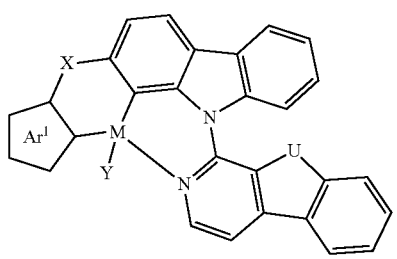
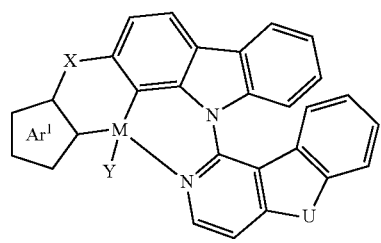
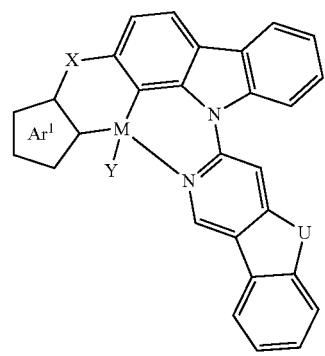
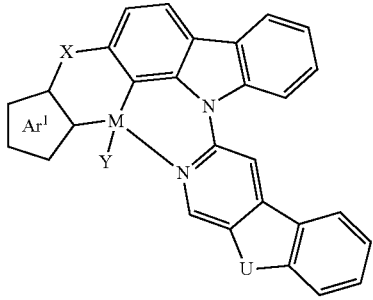
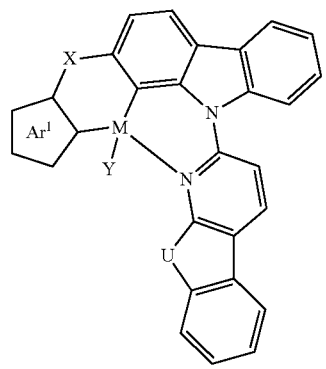
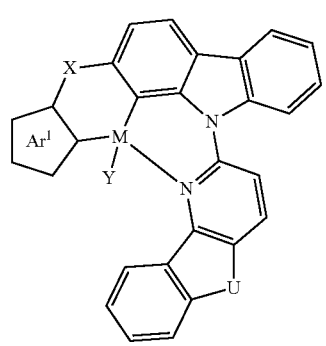
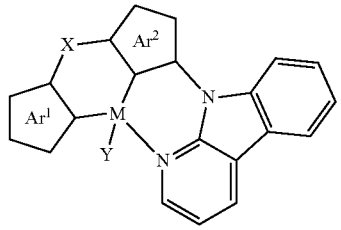
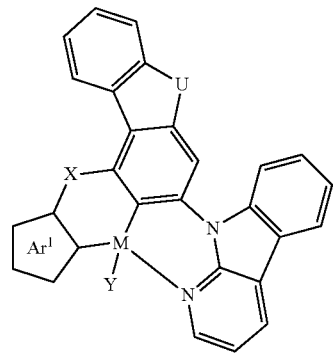

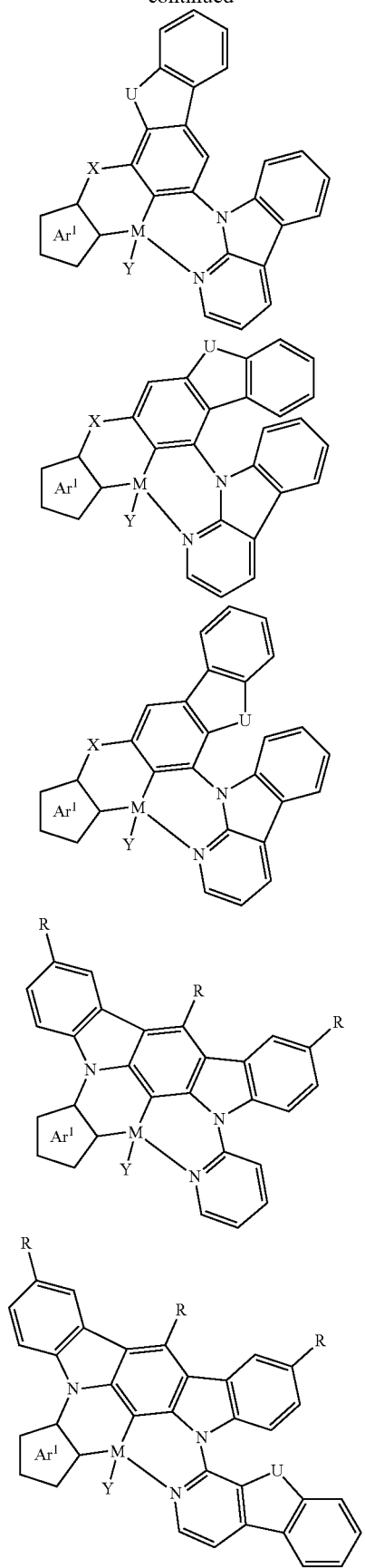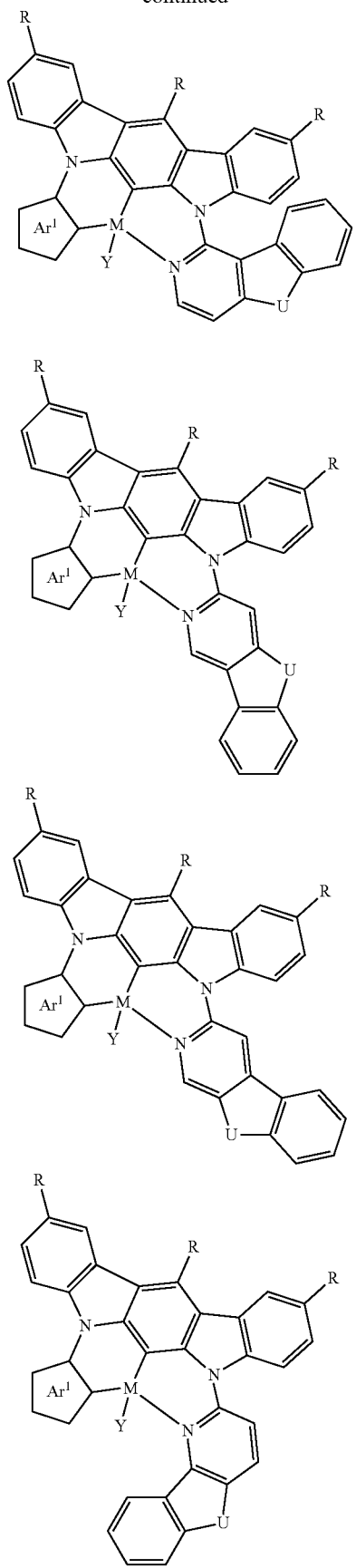

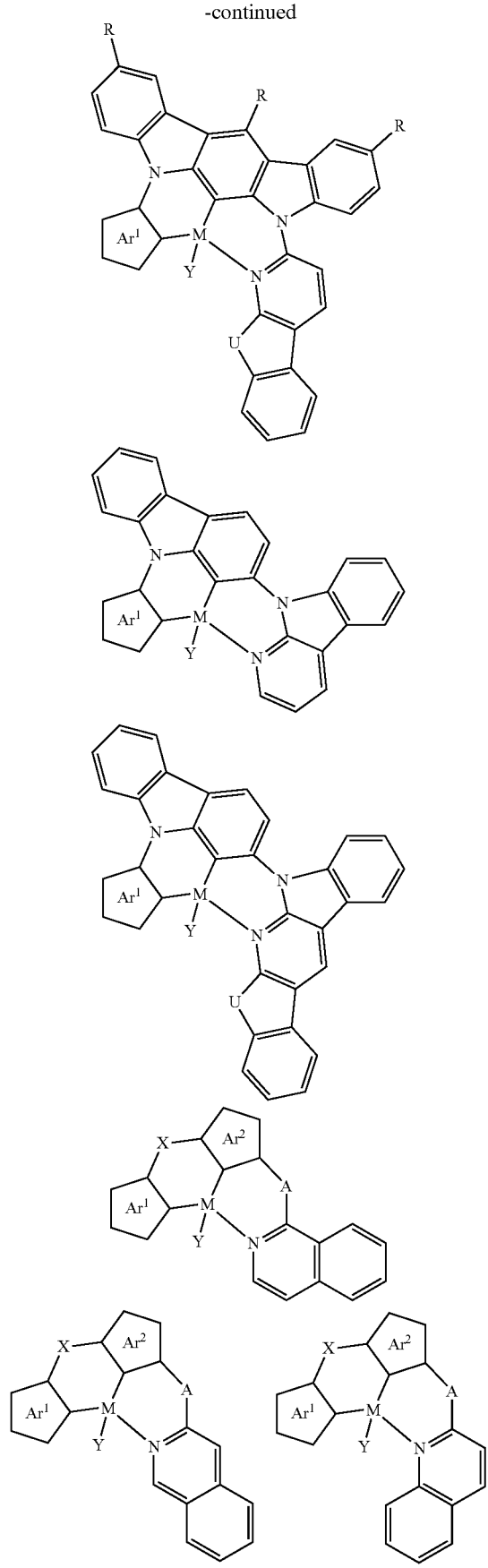
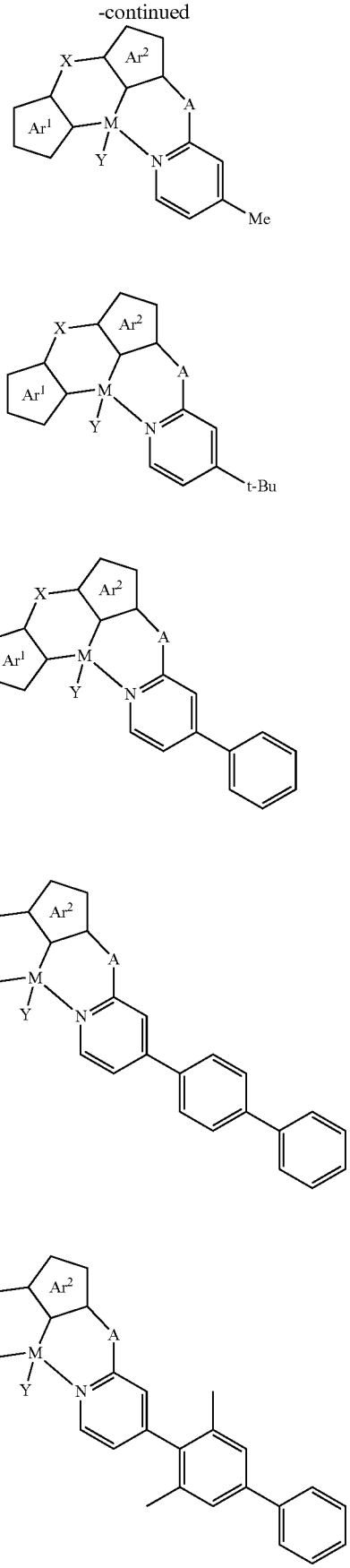

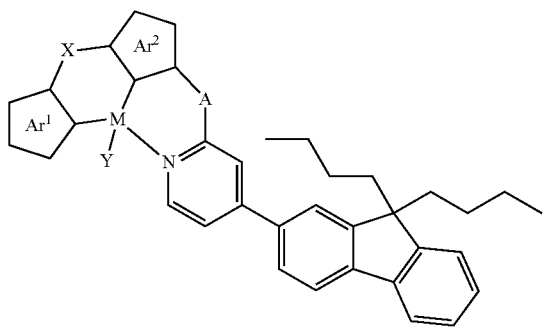
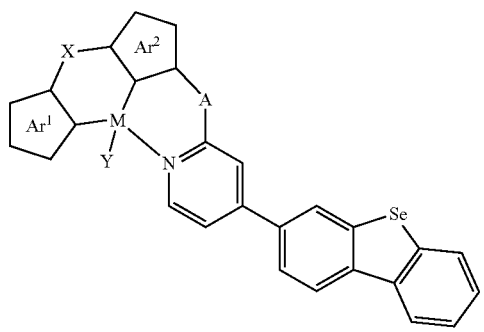
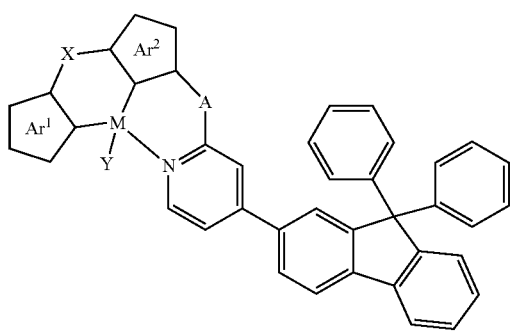
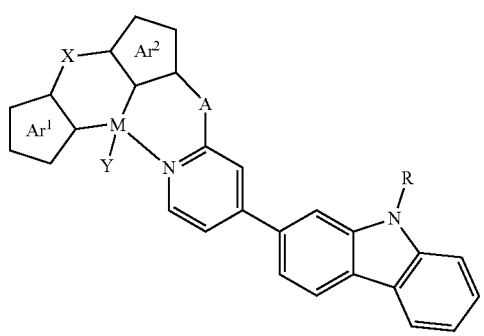
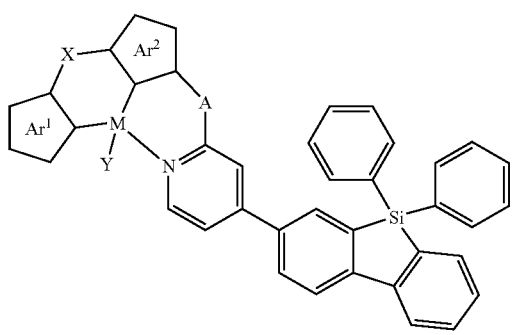
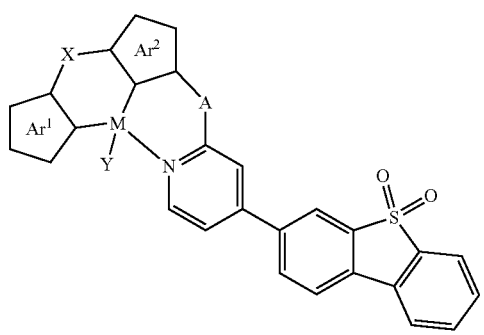
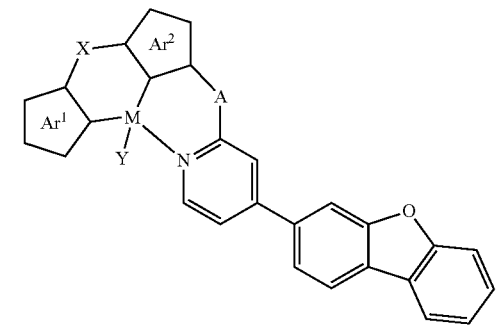
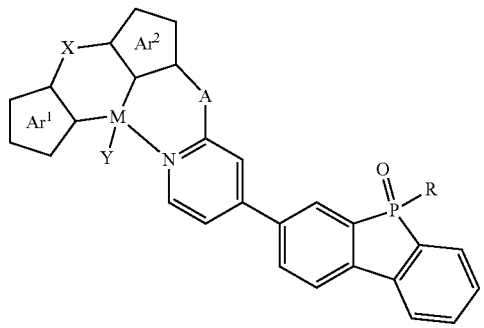
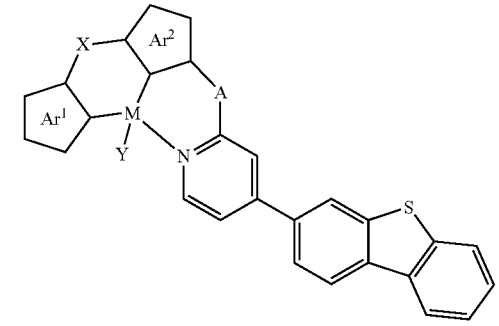
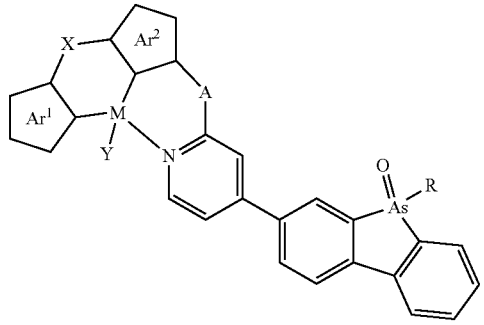

-continued

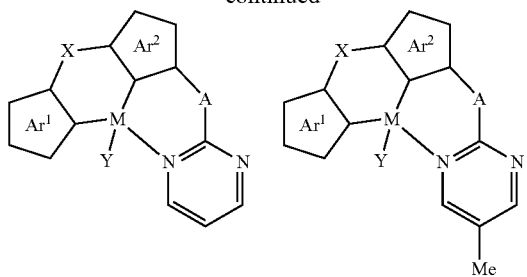

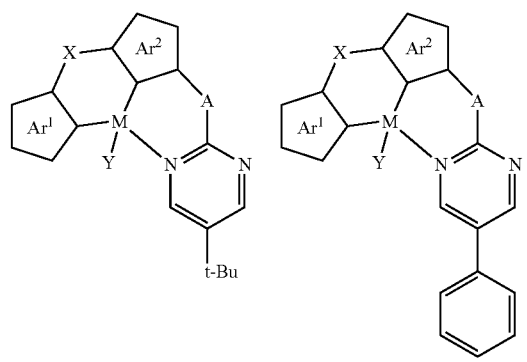

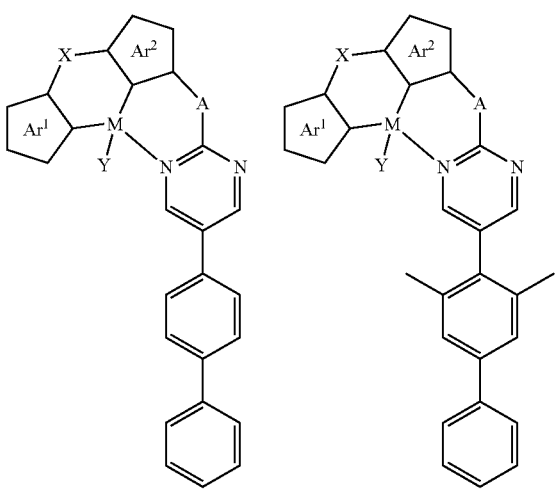

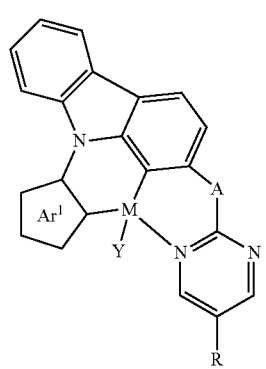

-continued

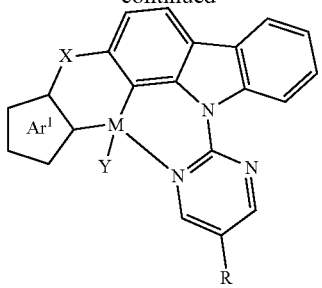

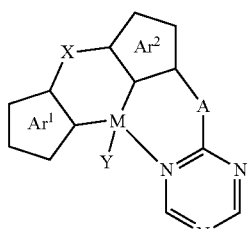
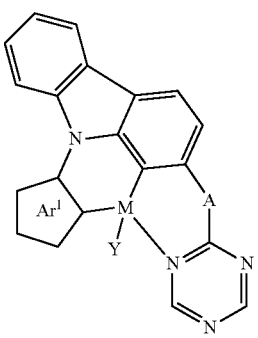

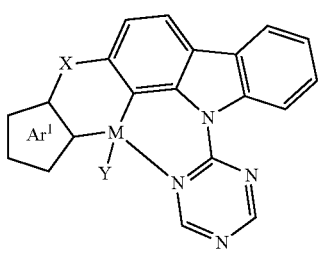

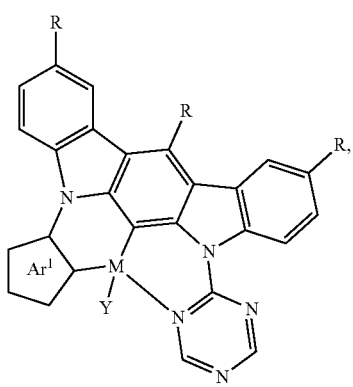

wherein:
X is O, S, NR, PR, AsR, CR₂, SiR₂, or BR.
A is O, S, NR, PR, AsR, CR₂, SiR₂, or BR.
U is O, S, NR, PR, AsR, CR₂, SiR₂, or BR.
M is Rh(I) or Ir(I), and
each R is independently hydrogen, halogen, substituted or unsubstituted: alkyl, alkenyl, alkynyl, or aryl, and
each of Ar¹ and Ar² independently represents substituted or unsubstituted five-membered heteroaryl or six-membered aryl or heteroaryl.

In addition, when
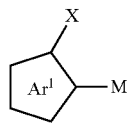
is one of
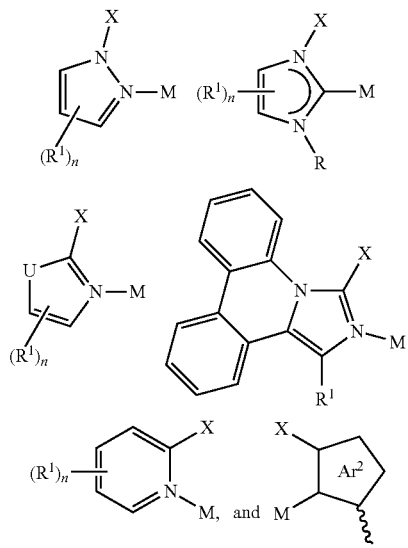
is one of
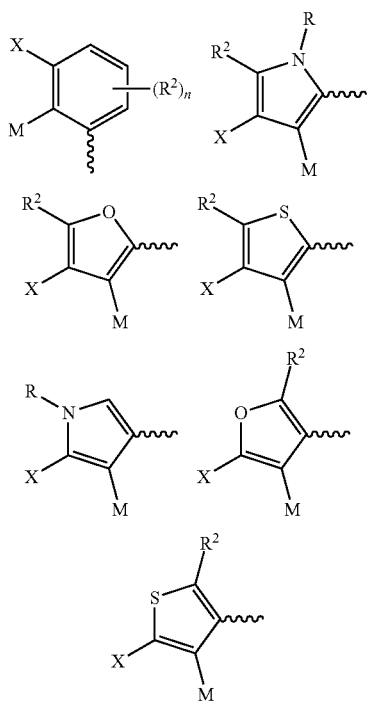
then
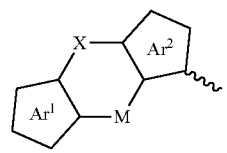
includes, but is not limited to, the following
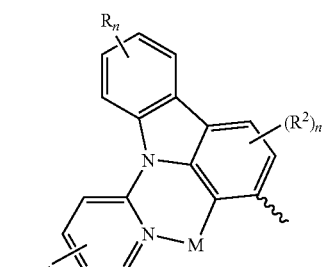
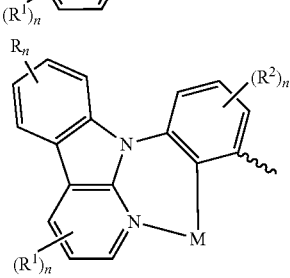
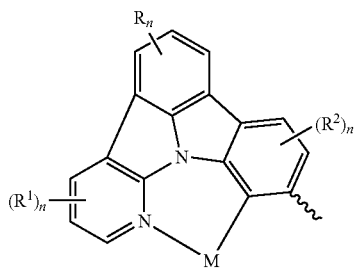
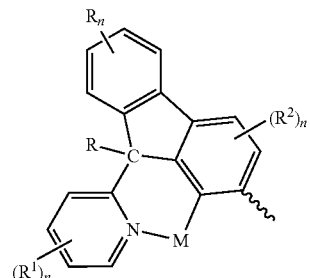
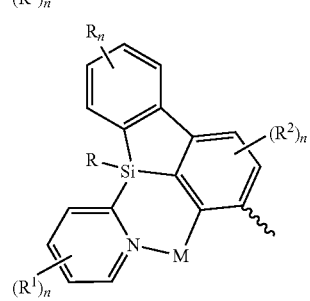

-continued
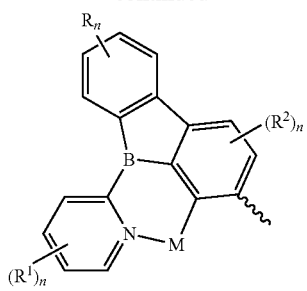
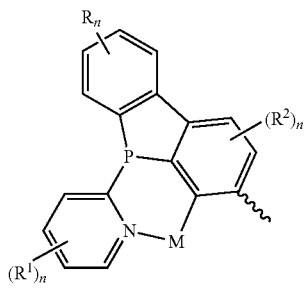
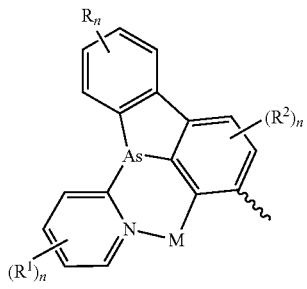
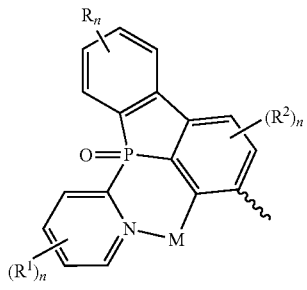
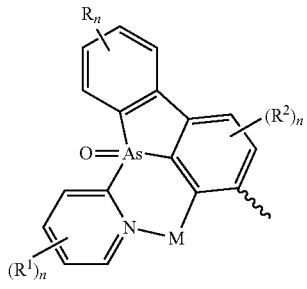
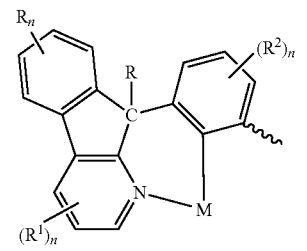
-continued
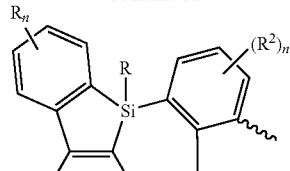
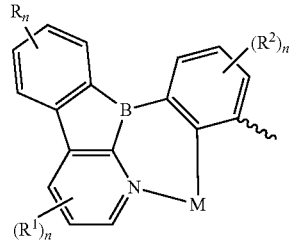
Y is CO, NR$_3$, PR$_3$, AsR$_3$, substituted or unsubstituted: pyridine, imidazole, or quinoline, and
each R is independently hydrogen, substituted or unsubstituted: alkyl, alkenyl, alkynyl, or aryl.
In one aspect, the complex of General Formula I has one of the following structures:
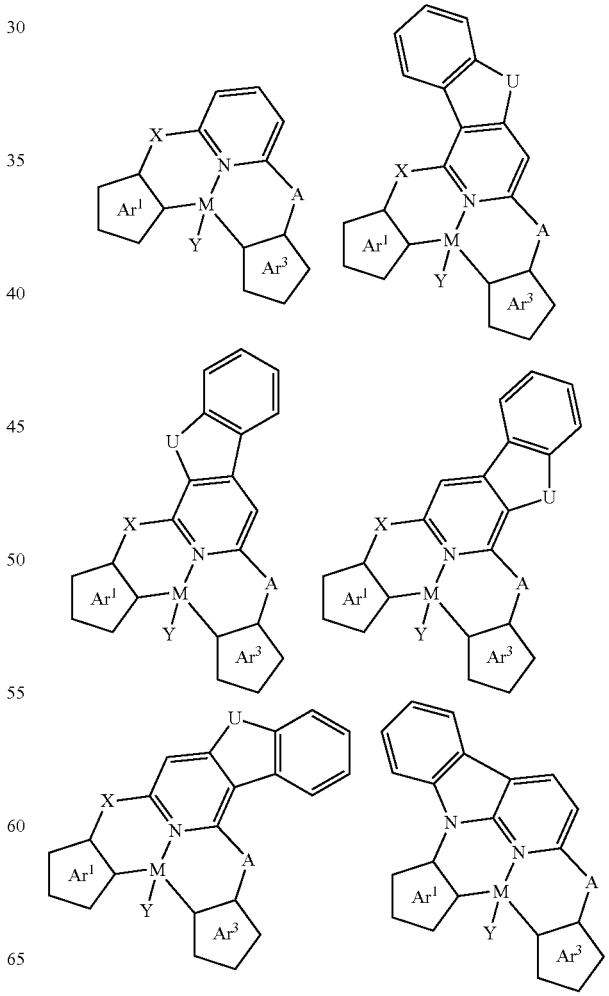

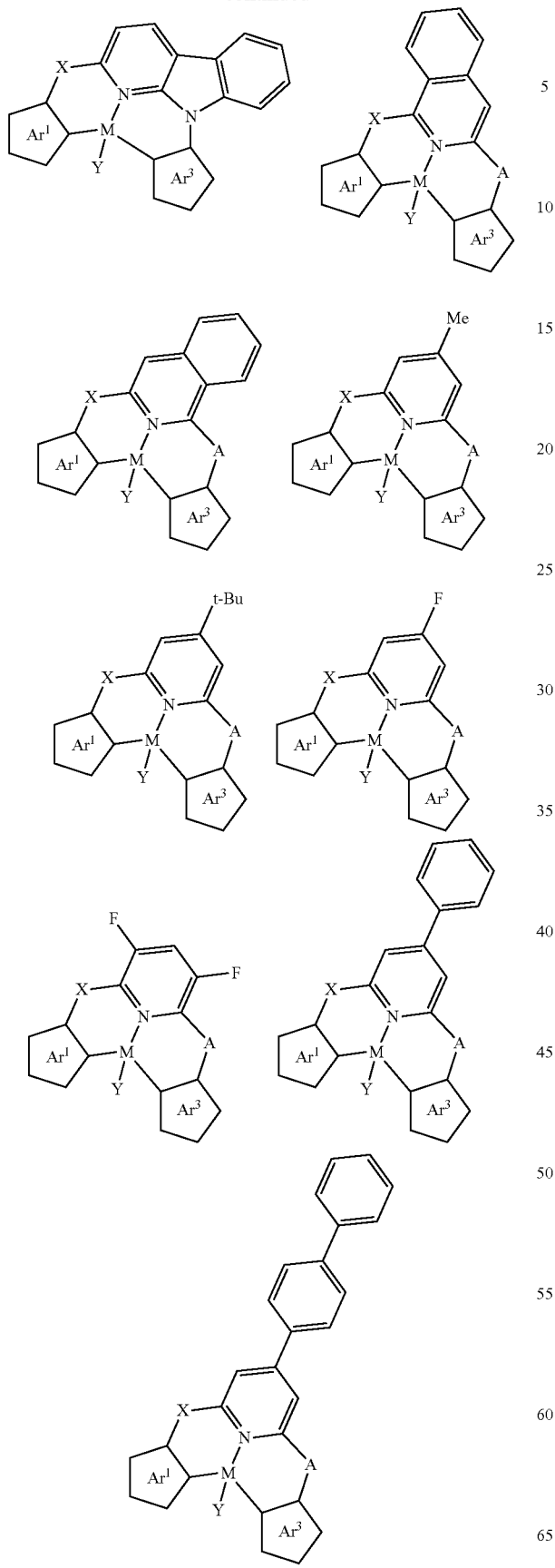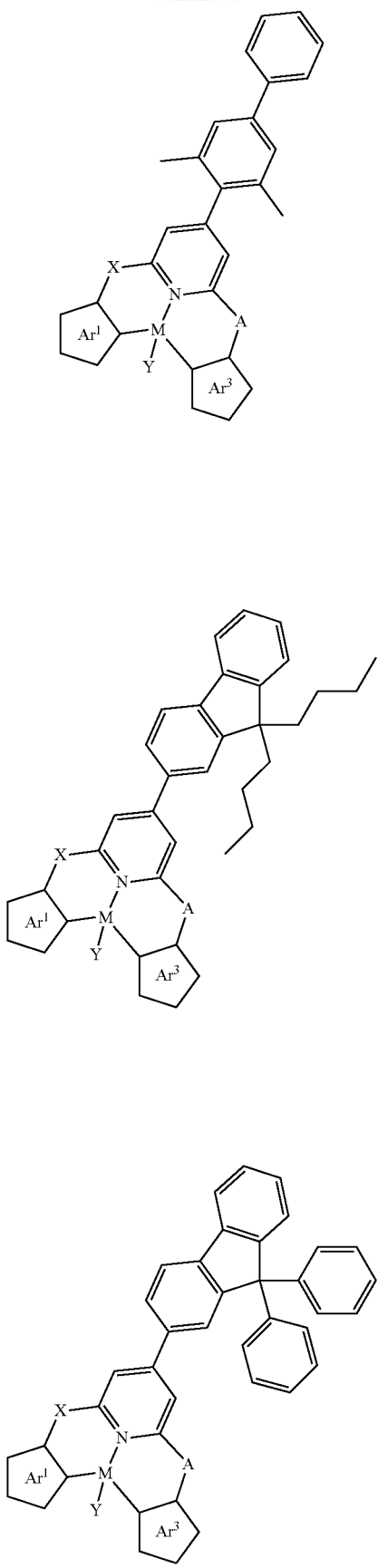

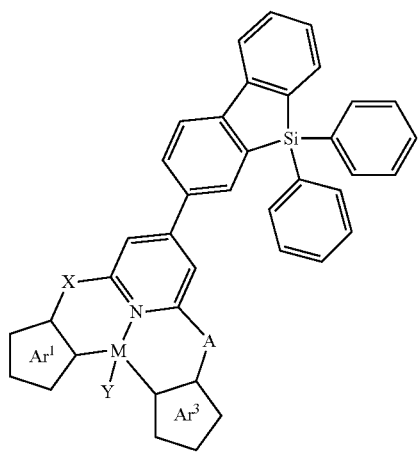
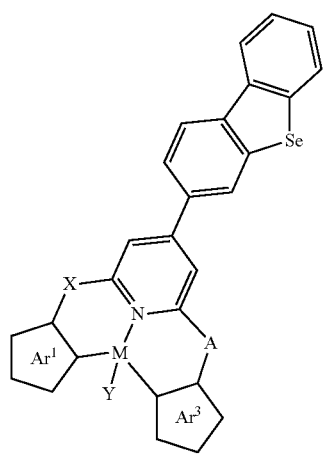
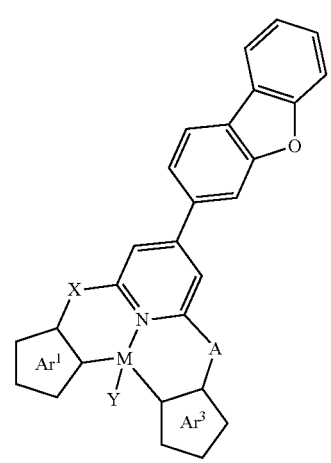
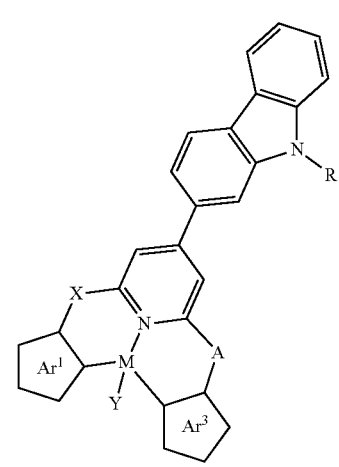
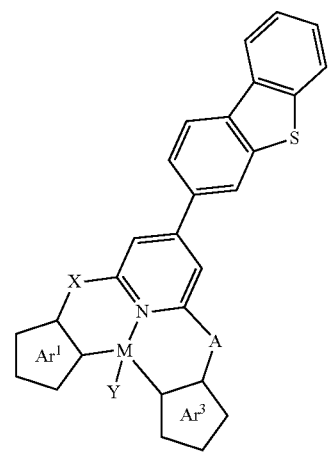
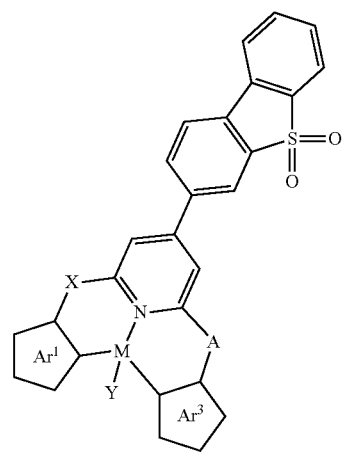

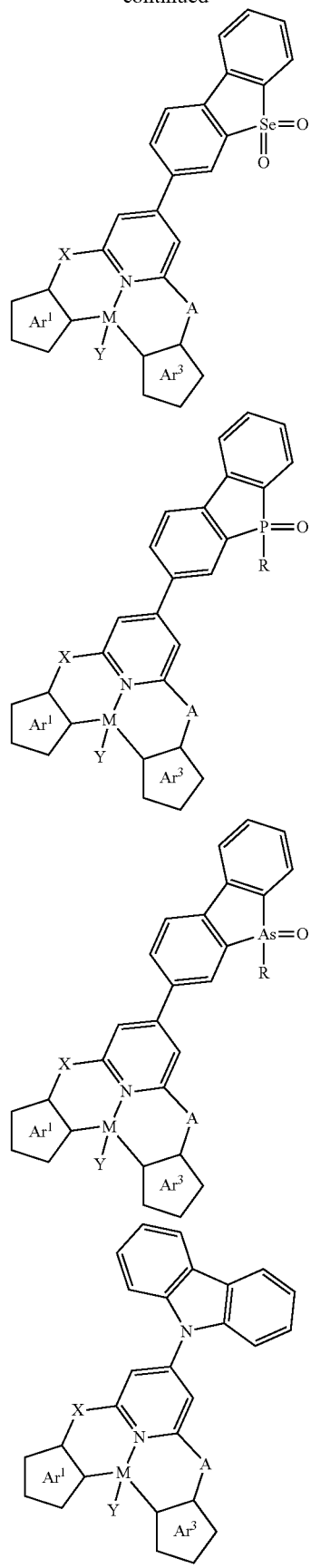
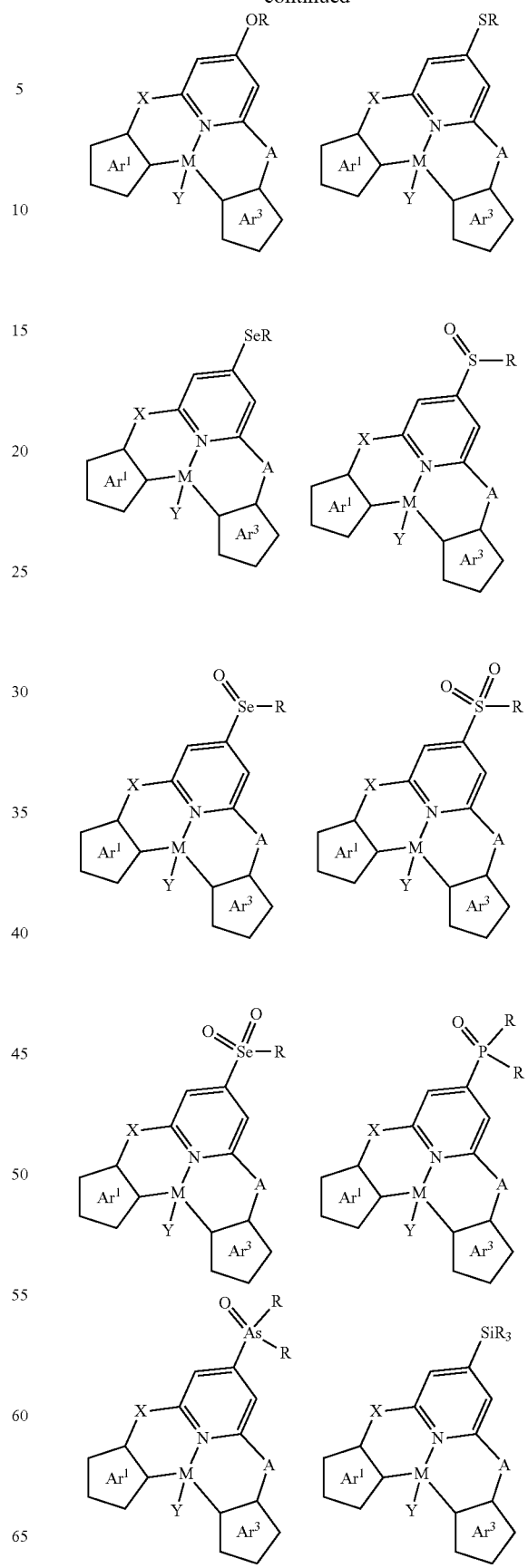

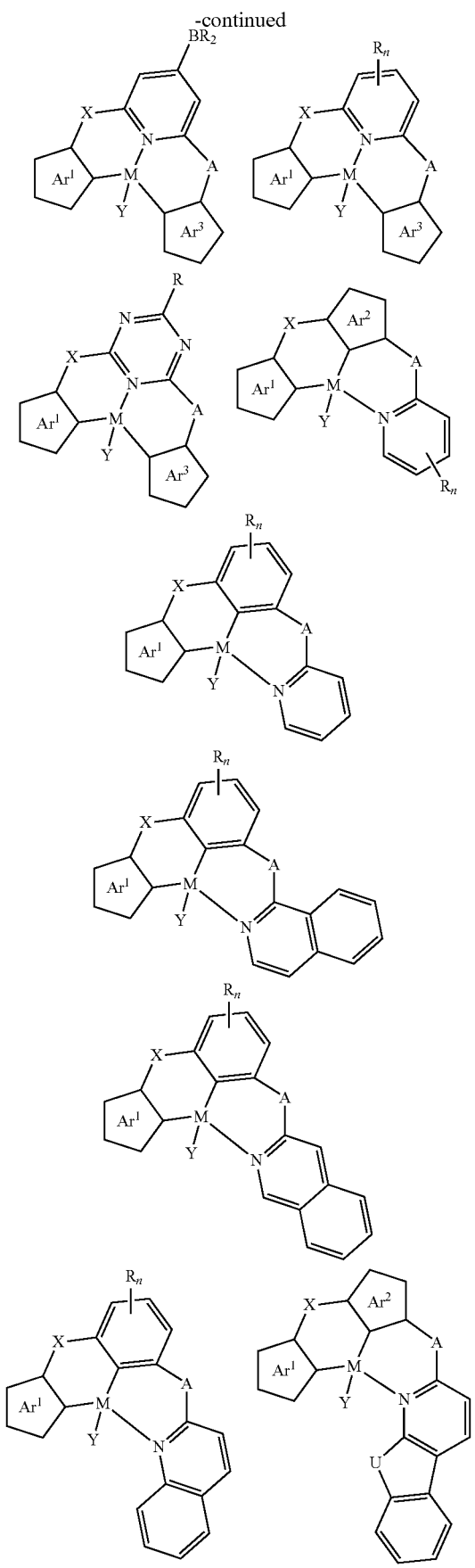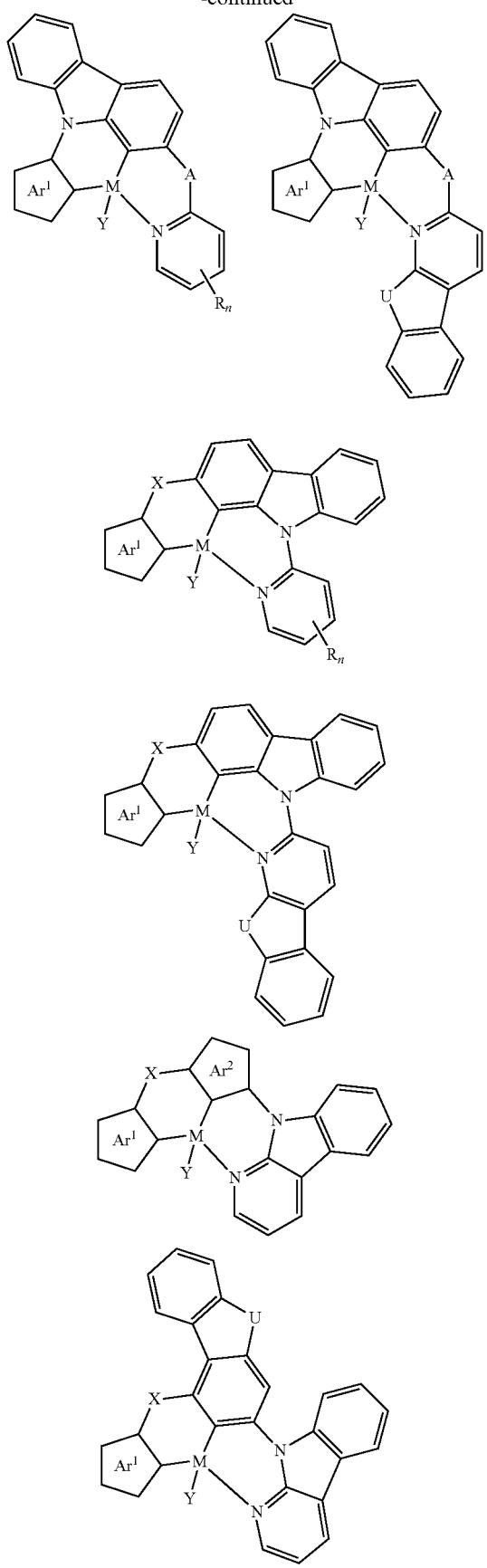

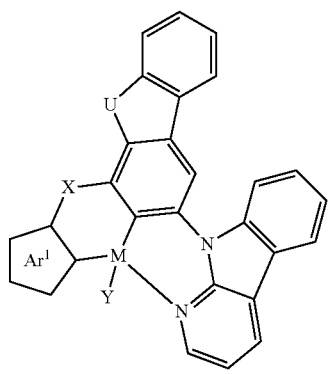
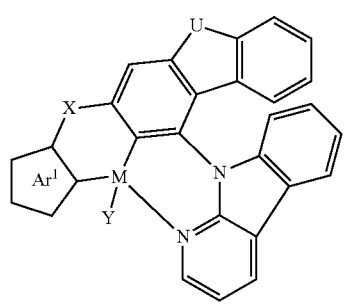
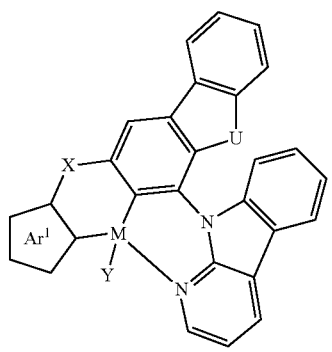
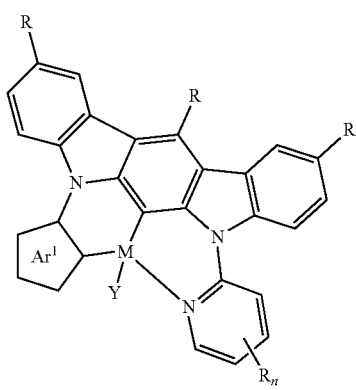
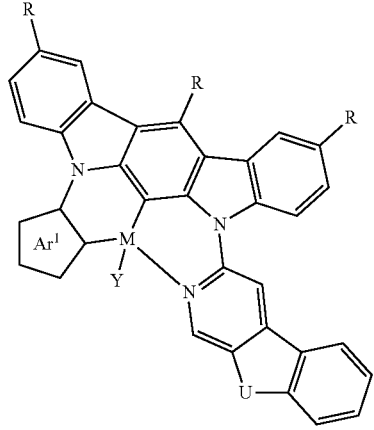
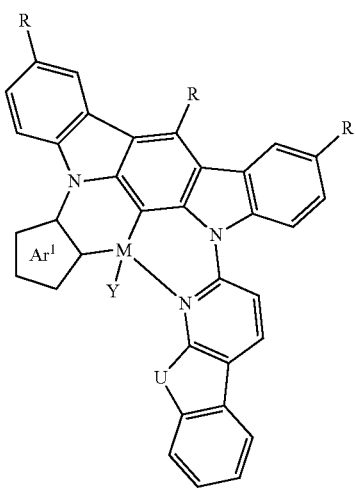
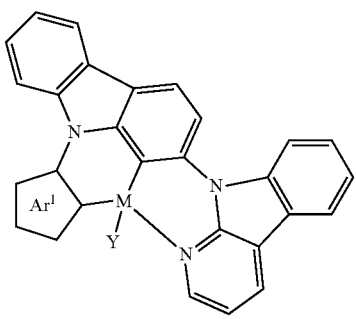
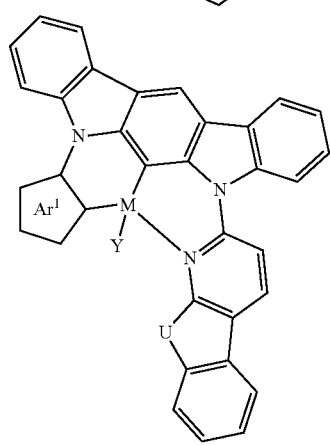

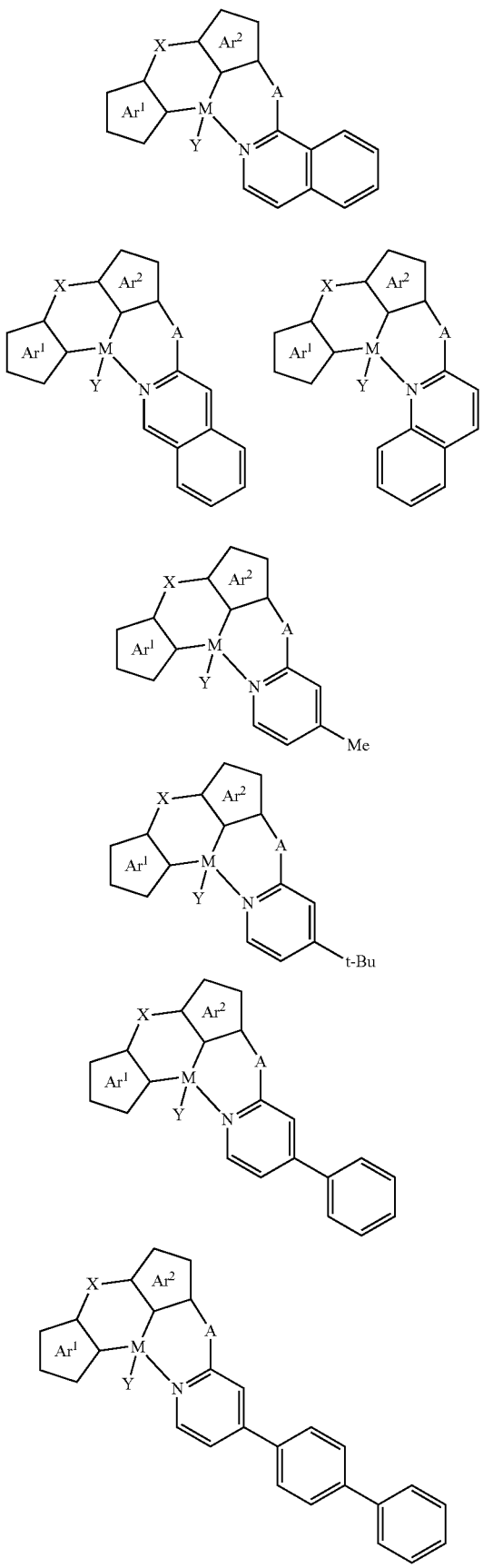
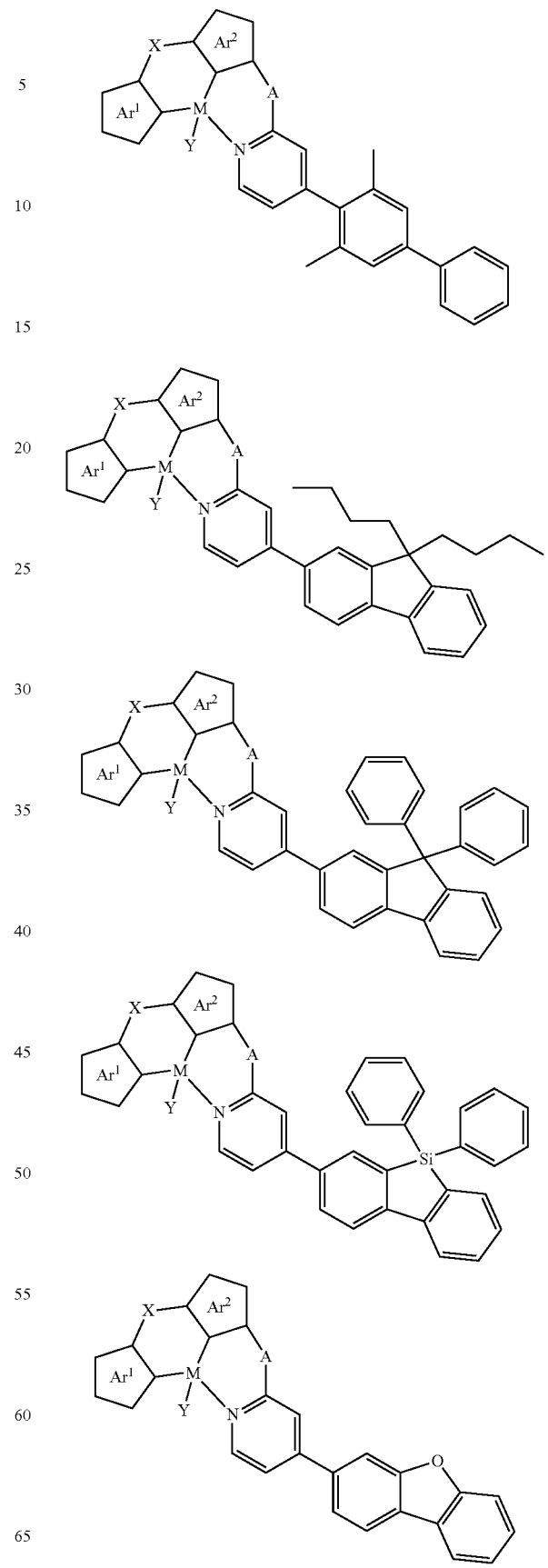

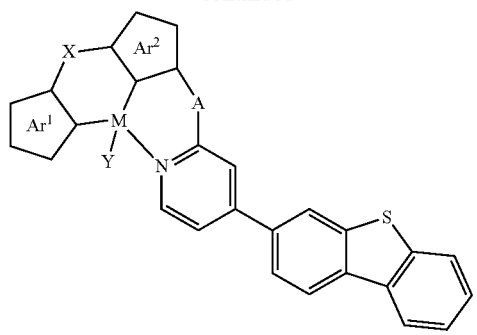
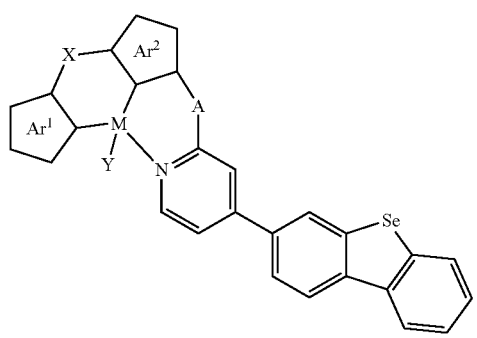
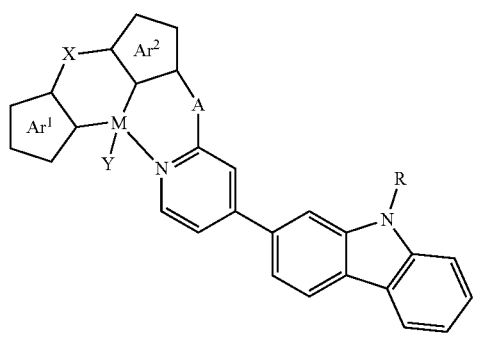
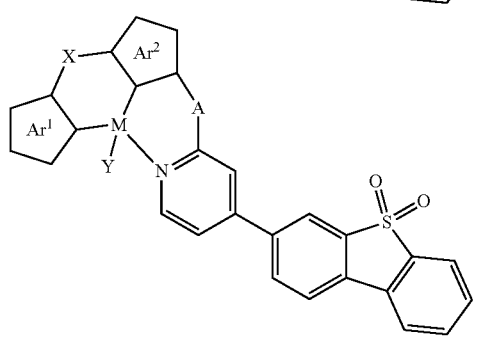
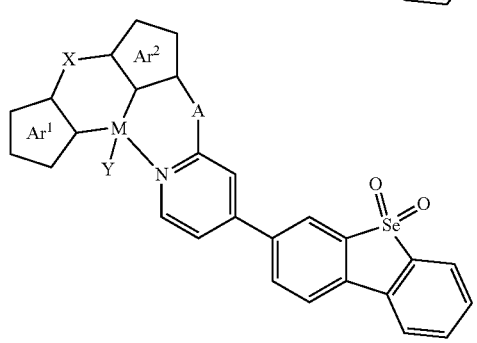
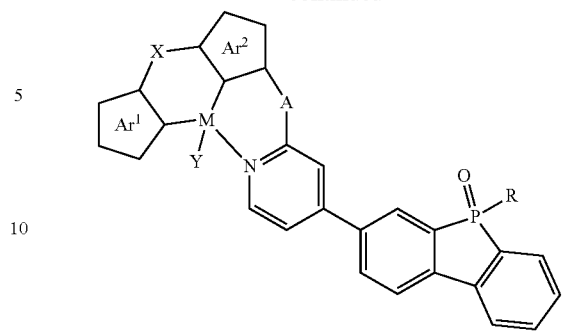
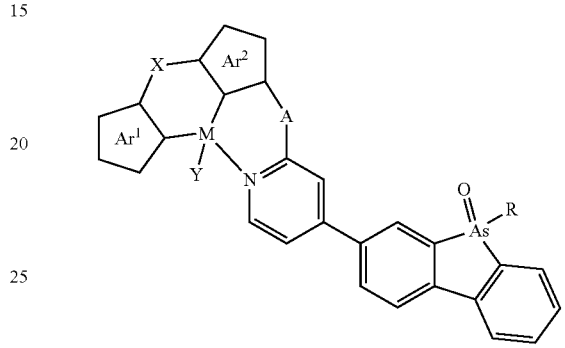
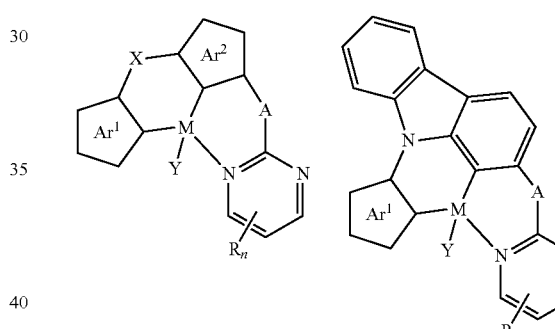
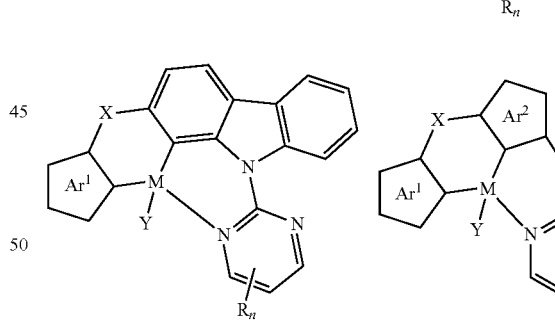
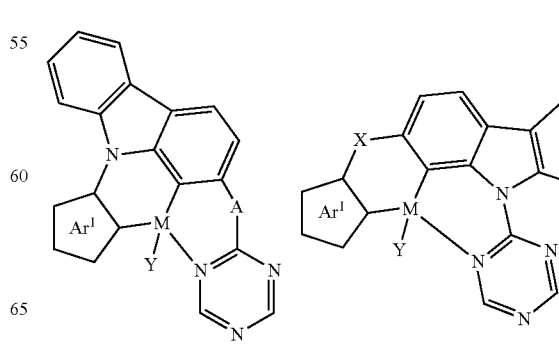

-continued

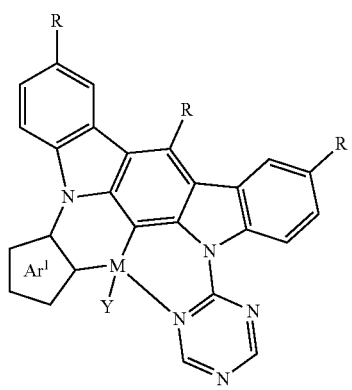

wherein:
X is O, S, NR, PR, AsR, CR$_2$, SiR$_2$, or BR.
A is O, S, NR, PR, AsR, CR$_2$, SiR$_2$, or BR.
U is O, S, NR, PR, AsR, CR$_2$, SiR$_2$, or BR.
M is Au(III),
each of Ar$^1$, Ar$^2$, and Ar$^3$ is independently substituted or unsubstituted five-membered heteroaryl or six-membered aryl or heteroaryl.
each R is independently hydrogen, halogen, substituted or unsubstituted: alkyl, alkenyl, alkynyl, or aryl.
In addition, when

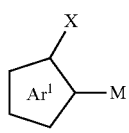

is one of

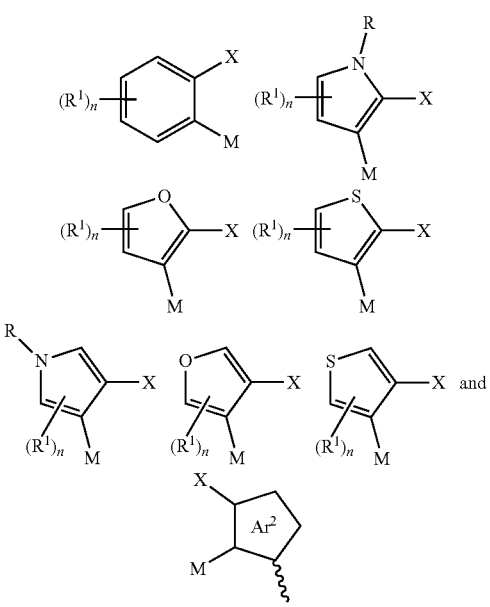

is one of

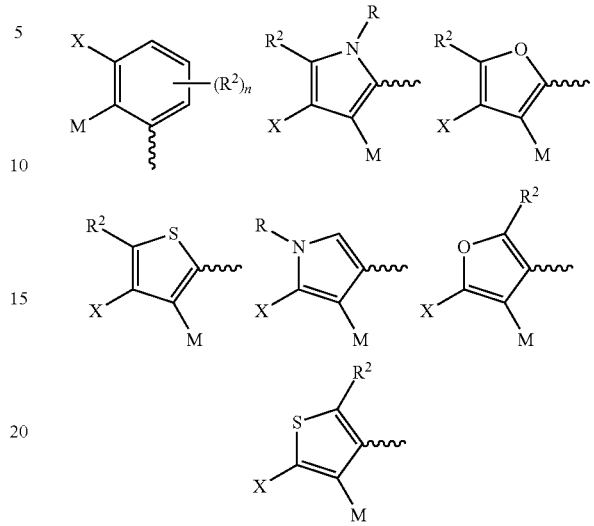

then

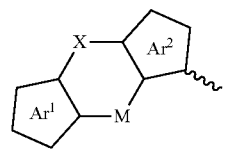

includes, but is not limited to, the following

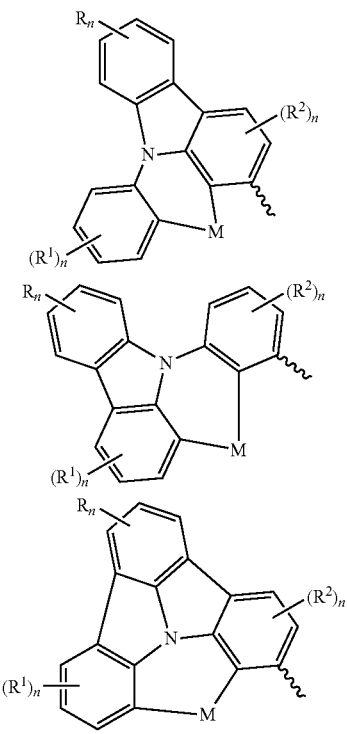

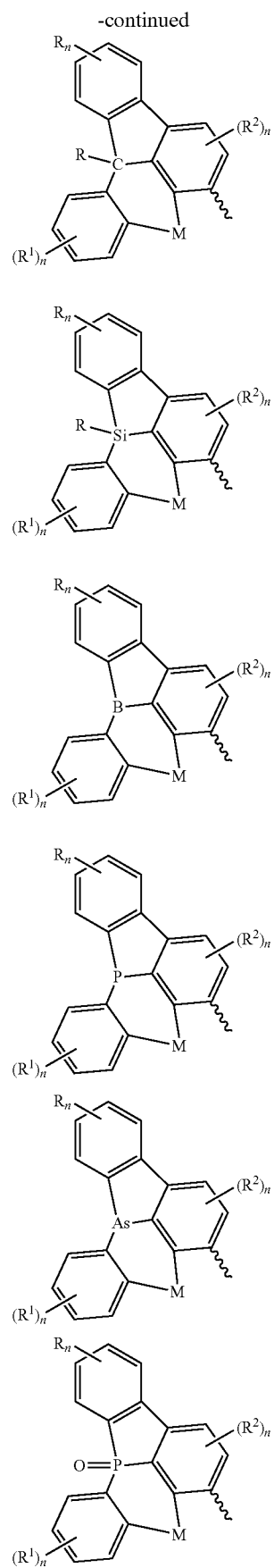

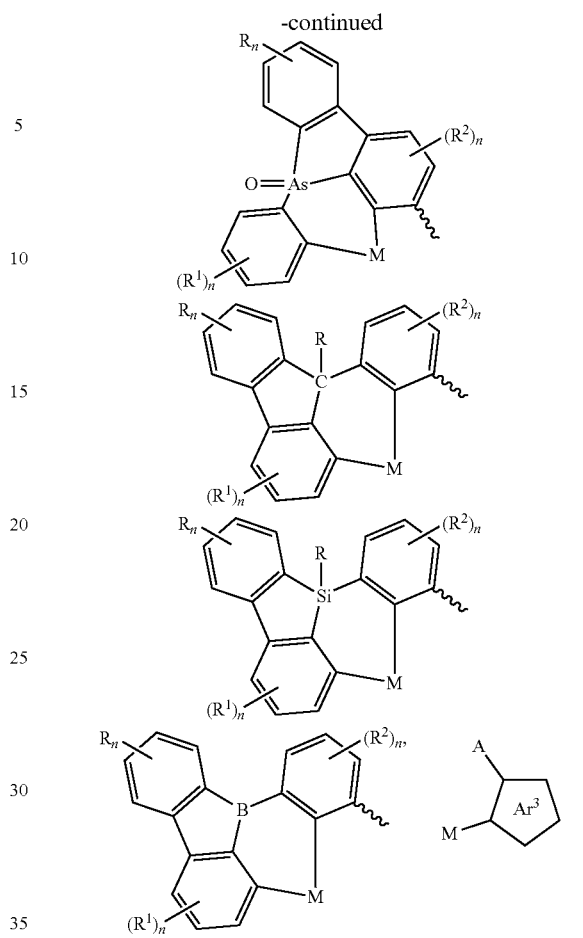

is one of

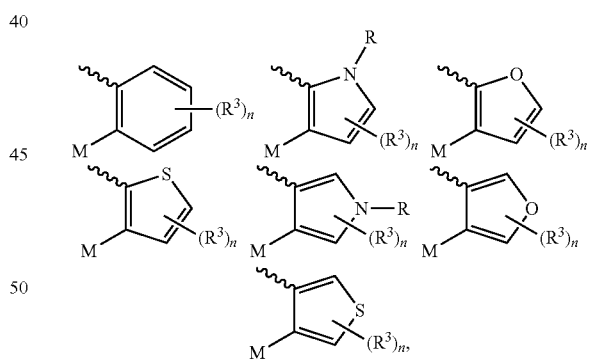

Y is Cl, Br, I, OR, OCOR, SR, NRR, or C≡CR, and each R is independently hydrogen, halogen, substituted or unsubstituted: alkyl, alkenyl, akynyl, or aryl.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications. Each device may include one or more compounds disclosed herein.

Compounds described herein can be used in an OLED. FIG. 1 depicts a cross-sectional view of an OLED 100.

OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds and/or the host material. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

The synthetic procedure for PtNNC1, depicted below, is exemplary for compounds of General Formula I. PtNNC1 has tridentate 6-membered coordination rings and a rigid molecular geometry.

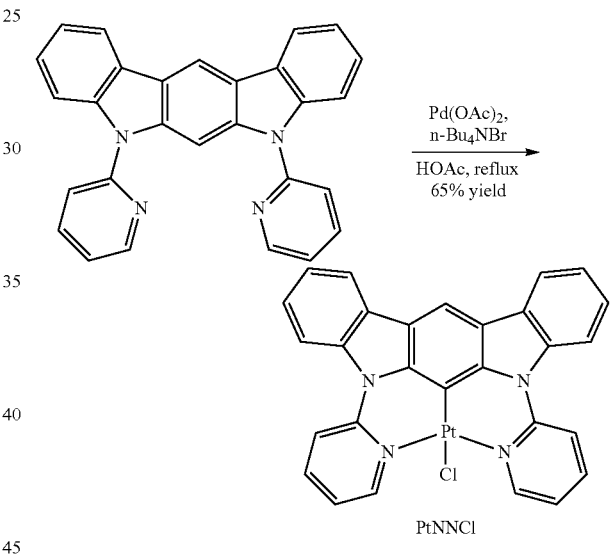

PtNNC1

Figure 2:
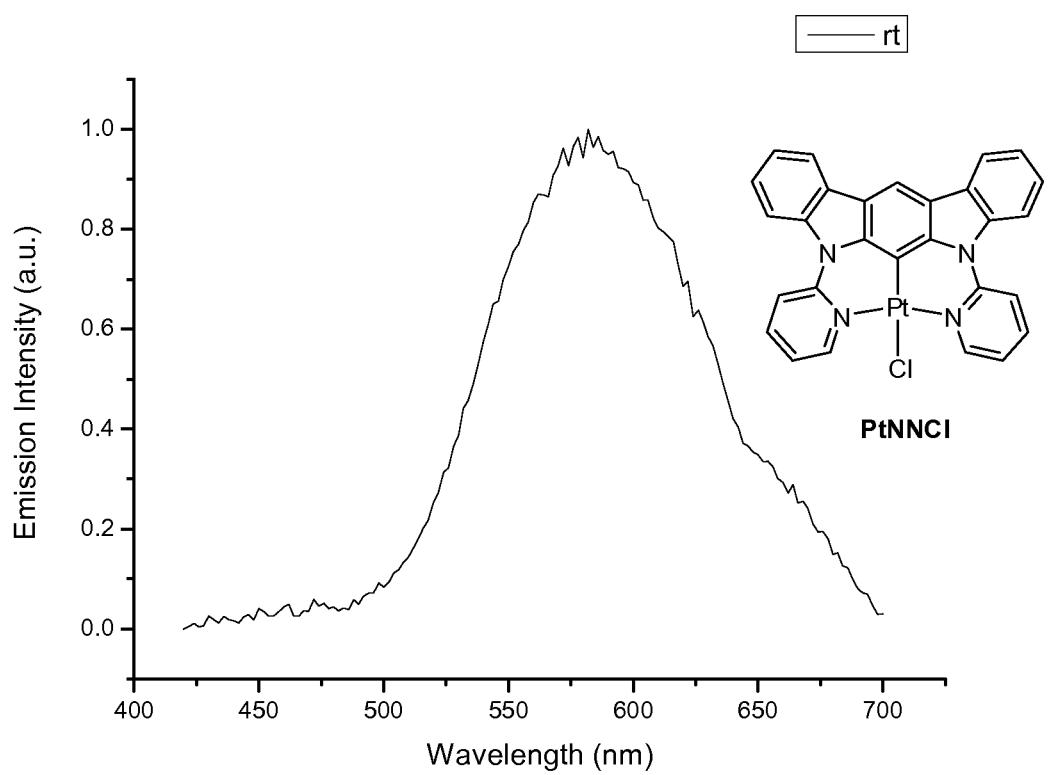
FIG. 2 shows a photoluminescence spectrum of PtNNC1 at room temperature.

PtNNC1 was prepared by the following procedure. To an oven-dried flask were added 5,7-di(pyridin-2-yl)-5,7-dihydroindolo[2,3-b]carbazole (74 mg, 0.18 mmol), K$_2$PtCl$_4$ (78 mg, 0.189 mmol), and n-Bu$_4$NBr (6 mg, 0.018 mmol). The flask was evacuated and backfilled with N$_2$, followed by the addition of HOAc (9 mL, 0.05 M) under the protection of N$_2$. The mixture was then heated at 120° C. After 2 days, the mixture was cooled to room temperature and concentrated under reduced pressure. Purification by flash column chromatography on silica gel (DCM/MeOH=20/1) gave PtNNC1 as a light yellow solid (75 mg, 65% yield). $^1$H NMR (DMSO-d$_6$, 400 MHz): $\delta$ 10.23 (d, J=5.1 Hz, 2H), 8.60 (s, 1H), 8.29 (d, J=7.9 Hz, 4H), 8.20 (d, J=7.9 Hz, 2H), 8.13 (t, J=7.8 Hz, 2H), 7.56 (t, J=7.6 Hz, 2H), 7.50 (t, J=7.5 Hz, 2H), 7.20 (t, J=6.7 Hz, 2H). MS (MALDI-TOF), m/z 604.39 (C$_{28}$H$_{17}$N$_4$Pt, [M-Cl]). A photoluminescence spectrum of PtNNC1 at room temperature is shown in FIG. 2.

What is claimed is:

1. A complex represented by Formula 3:

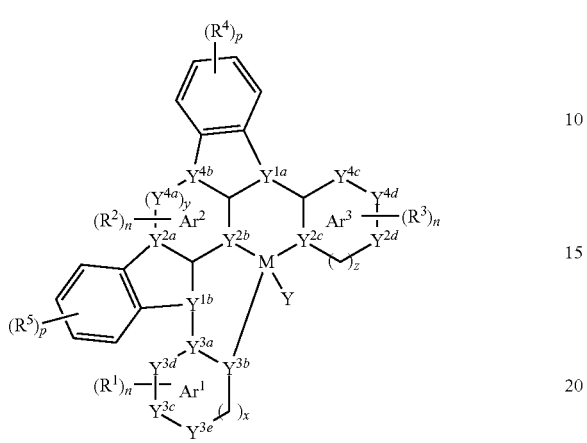

Formula 3 wherein:

M is Pt(II), Pd(II), Ir(I), Rh(I), or Au(II), x is 1;

y is 1;

z is 1;

each n is independently an integer of 1 to 4, valency permitting, each $R^1$, $R^2$, and $R^3$ is independently hydrogen, halogen, hydroxyl, amino, nitro, thiol, or substituted or unsubstituted alkyl, alkoxyl, alkenyl, alkynyl, heteroaryl, or aryl; and any two of $R^1$, any two of $R^2$, and any two of $R^3$ are optionally linked together;

$Y^{1a}$ is N;

$Y^{1b}$ is N;

$Y^{3b}$ is N;

$Y^{3a}$ is C;

$Y^{3c}$, $Y^{3d}$, and $Y^{3e}$ are C or N;

$Y^{2c}$ is N;

$Y^{2d}$, $Y^{4c}$, and $Y^{4d}$ are C or N;

$Y^{2b}$, $Y^{4b}$, and $Y^{2a}$ are C;

$Y^{4a}$ is C or N;

$Ar^1$, $Ar^2$, and $Ar^3$ are aromatic;

Y is halogen, $OCOR^{7a}$, $OR^{7b}$, $SR^{7c}$, $NR^{7d}R^{7e}$, CO, $NR^{7f}$, $PR^{7g}$, $AsR^{7h}R^{7i}R^{7j}$, $C\equiv CR^{7k}$, substituted or unsubstituted: pyridine, imidazole, pyrazole, oxazole, thiazole, isoxazole, or quinoline, where each of $R^{7a}$, $R^{7b}$, $R^{7c}$, $R^{7d}$, $R^{7e}$, $R^{7f}$, $R^{7g}$, $R^{7h}$, $R^{7i}$, $R^{7j}$, and $R^{7k}$ is independently acetylacetonate, pyridine, imidazole or substituted or unsubstituted alkyl, alkenyl, alkynyl, aryl, or trisubstituted phosphine;

p is 4;

each $R^4$ and $R^5$ is independently hydrogen, halogen, hydroxyl, amino, nitro, thiol, or substituted or unsubstituted alkyl, alkoxyl, alkenyl, alkynyl, heteroaryl, or aryl;

any two of $R^4$ are optionally linked together; and any two of $R^5$ are optionally linked together.

2. The complex of claim 1, wherein the complex is represented by one of the following structures:

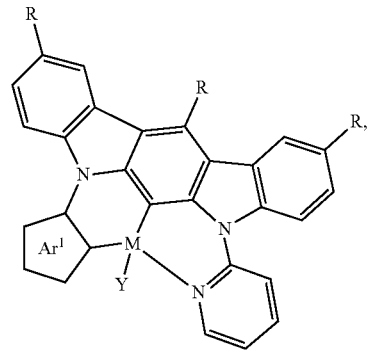

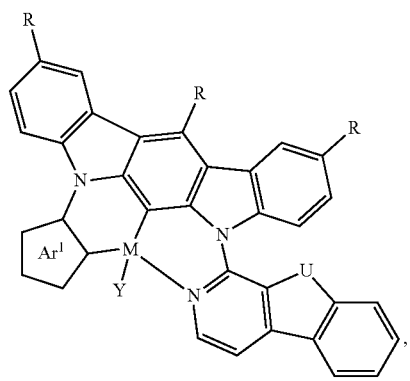

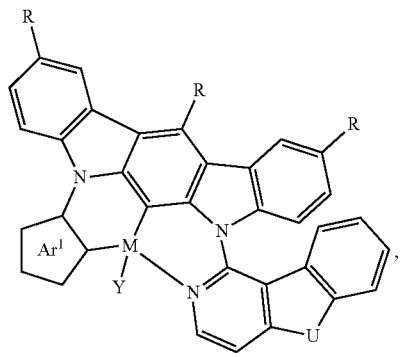

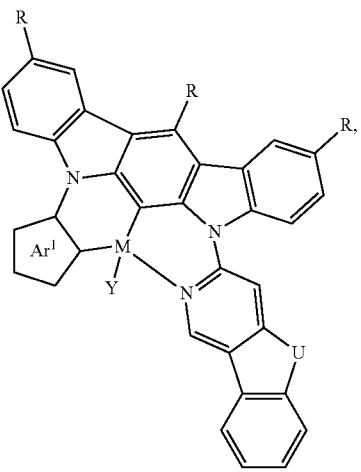

-continued

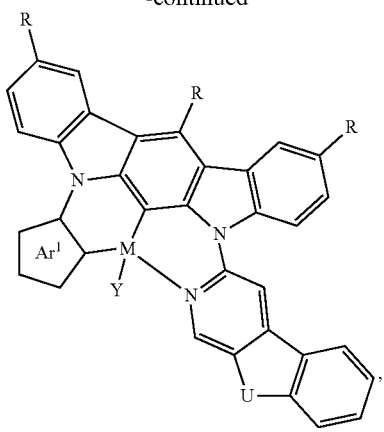

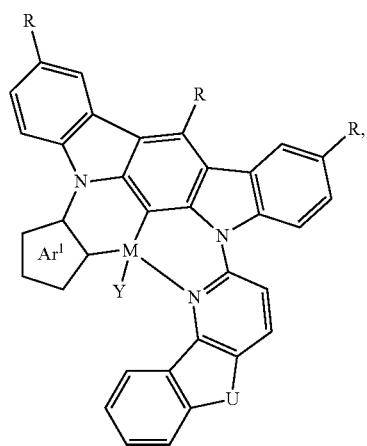

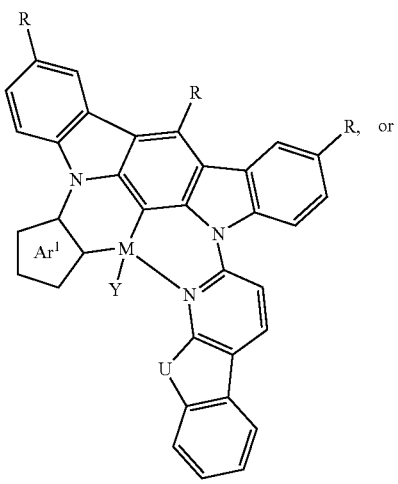

-continued

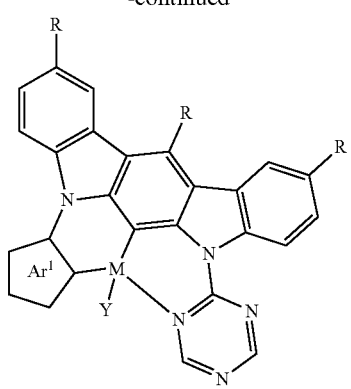

wherein:
U is O, S, NR, PR, AsR, $CR_2$, $SiR_2$, or BR;
M is Pt(II) or Pd(II);
each R is independently hydrogen, halogen, or substituted or unsubstituted alkyl, alkenyl, alkynyl, or aryl; and
each $Ar^1$ is independently selected from the group consisting of 6-membered substituted or unsubstituted heteroaryl.

3. The complex of claim 1, wherein the complex is represented by one of the following structures:

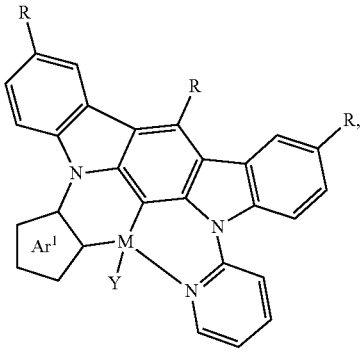

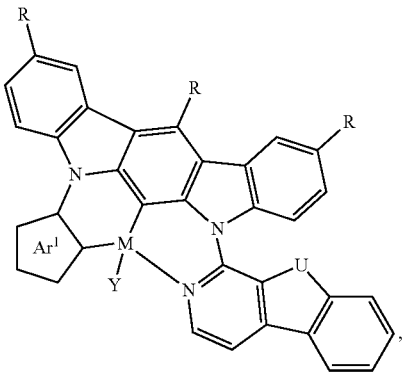

81
-continued

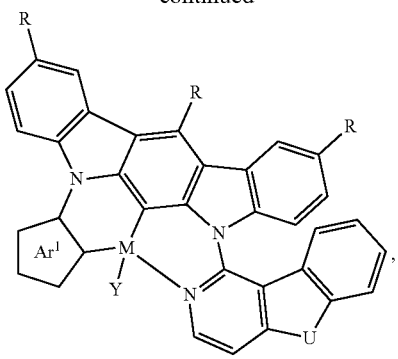

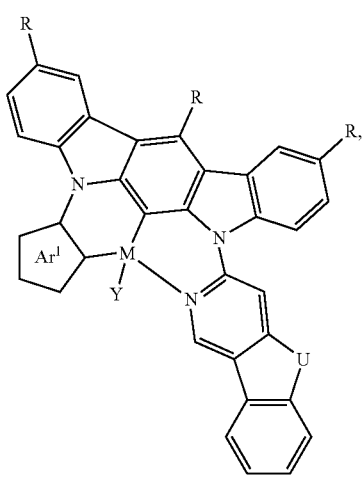

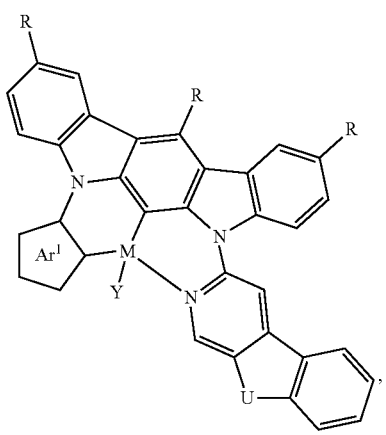

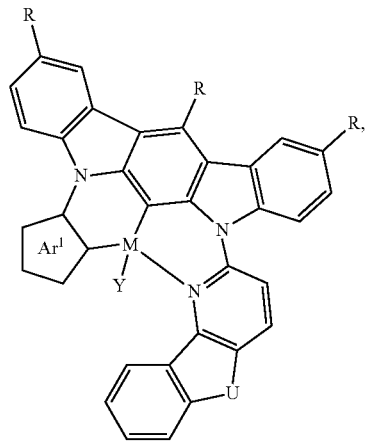

82
-continued

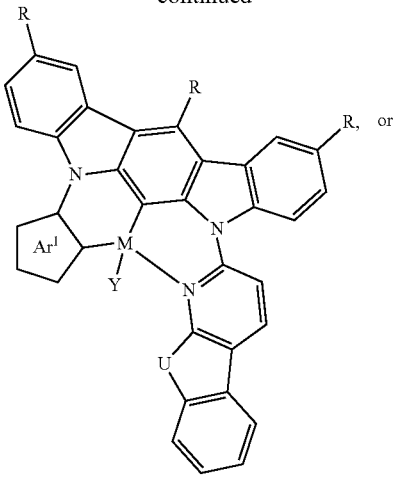

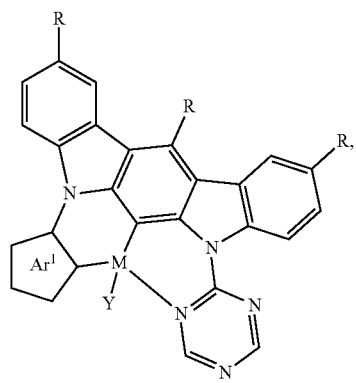

wherein:
U is O, S, NR, PR, AsR, $CR_2$, $SiR_2$, or BR;
M is Rh(I) or Ir(I);
each R is independently selected from the group consisting of hydrogen, halogen, or substituted or unsubstituted alkyl, alkenyl, alkynyl, or aryl; and
each $Ar^1$ is 6-membered substituted or unsubstituted heteroaryl.

4. The complex of claim 1, wherein the complex is represented by one of the following structures:

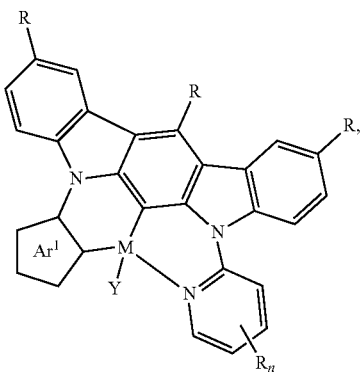

-continued

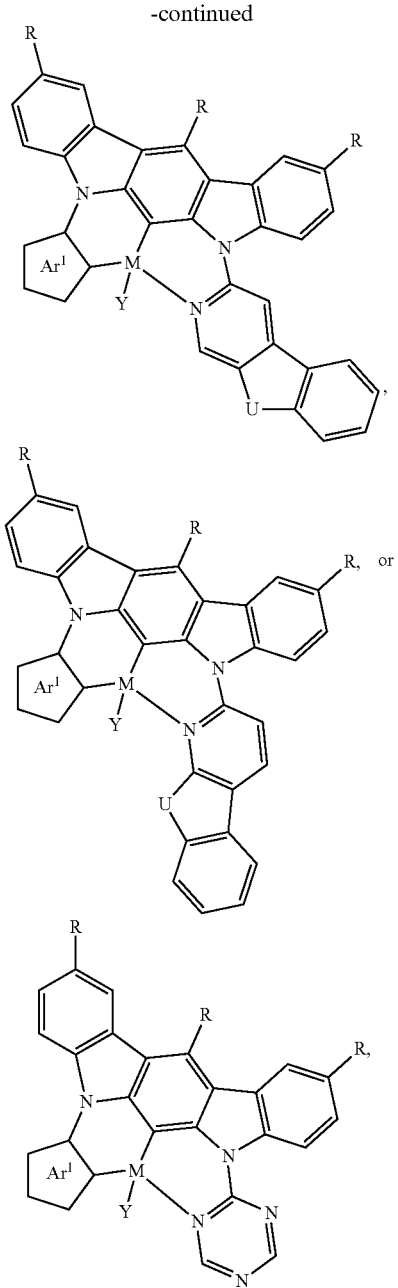

wherein:
U is O, S, NR, PR, AsR, CR₂, SiR₂, or BR;
M is Au(III);
each R is independently hydrogen, halogen, substituted or unsubstituted alkyl, alkenyl, alkynyl, or aryl;
n is an integer of 1 to 4; and
each $Ar^1$ is independently 6-membered substituted or unsubstituted heteroaryl.

5. A light emitting device comprising the complex of claim 1.

6. An OLED device comprising the complex of claim 1.

7. The OLED device of claim 6, wherein the device is a phosphorescent OLED device.

8. A photovoltaic device comprising the complex of claim 1.

9. A luminescent display device comprising the complex of claim 1.

10. The complex of claim 1, wherein the complex has the structure:

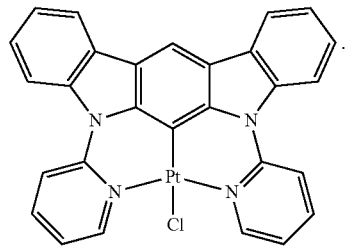

11. The complex of claim 1, wherein M is Pt(II).

12. The complex of claim 1, wherein $R^1$, $R^2$, and $R^3$ are each independently hydrogen, halogen, hydroxyl, amino, or substituted or unsubstituted alkyl.

13. The complex of claim 1, wherein $R^1$, $R^2$, and $R^3$ are hydrogen.

14. The complex of claim 1, wherein Y is halogen, $OCOR^{7a}$, $OR^{7b}$, $SR^{7c}$, $NR^{7d}R^{7e}$, CO, $NR^{7f}$, $PR^{7g}$, $AsR^{7h}R^{7i}R^{7j}$, or $C\equiv CR^{7k}$.

15. The complex of claim 1, wherein Y is halogen.

16. The complex of claim 1, wherein $R^4$ and $R^5$ are hydrogen.

17. The complex of claim 2, wherein
M is Pd(II);
each R is independently hydrogen; and
each $Ar^1$ is independently 6-membered unsubstituted heteroaryl.

* * * * *

UNITED STATES PATENT AND TRADEMARK OFFICE
CERTIFICATE OF CORRECTION

PATENT NO. : 9,502,671 B2
APPLICATION NO. : 14/808190
DATED : November 22, 2016
INVENTOR(S) : Jian Li and Zhi-Qiang Zhu Page 1 of 1

It is certified that error appears in the above-identified patent and that said Letters Patent is hereby corrected as shown below:

In Column 77, In Line 41, In Claim 1, delete "C:" and insert -- C; --, therefor.

In Column 77, In Line 58 (approx.), In Claim 1, delete "4:" and insert -- 4; --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*